US009606046B2

(12) United States Patent
Decaux et al.

(10) Patent No.: US 9,606,046 B2
(45) Date of Patent: Mar. 28, 2017

(54) IMAGING METHOD AND SYSTEM FOR ANALYZING IN-VITRO BIOLOGICAL SAMPLES

(75) Inventors: Dominique Decaux, Chaponost (FR);
Frédéric Pinston, Grenoble (FR);
Denis Desseree, Montluel (FR);
Guillaume Boissier, Lyons (FR);
Corine Fulchiron, Serrières de Briord (FR); Lorette Lapierre, Ambronay (FR); Lorène Allano, Sèvres (FR);
Léontine Jacolin, Paris (FR);
Christophe Tachier, Lyons (FR)

(73) Assignee: bioMérieux, Marcy l'Etoile (FR)

( * ) Notice: Subject to any disclaimer, the term of this patent is extended or adjusted under 35 U.S.C. 154(b) by 269 days.

(21) Appl. No.: 14/115,802

(22) PCT Filed: May 7, 2012

(86) PCT No.: PCT/EP2012/058398
§ 371 (c)(1),
(2), (4) Date: Feb. 27, 2014

(87) PCT Pub. No.: WO2012/152768
PCT Pub. Date: Nov. 15, 2012

(65) Prior Publication Data
US 2014/0293036 A1    Oct. 2, 2014

(30) Foreign Application Priority Data
May 6, 2011    (EP) .................................... 11305542

(51) Int. Cl.
*G06T 7/00*    (2006.01)
*G01N 21/01*    (2006.01)
(Continued)

(52) U.S. Cl.
CPC ............. *G01N 21/01* (2013.01); *G01N 21/17* (2013.01); *G01N 21/255* (2013.01); *G01N 21/27* (2013.01);
(Continued)

(58) Field of Classification Search
CPC ...... G01N 21/01; G01N 21/17; G01N 21/255; G01N 2201/0626; G06T 7/0012
See application file for complete search history.

(56) References Cited

U.S. PATENT DOCUMENTS 3,551,019 A    12/1970    Michel
5,580,163 A    12/1996    Johnson, II
(Continued)

FOREIGN PATENT DOCUMENTS

CN    1677088 A    10/2005
CN    101072993 A    11/2007
(Continued)

OTHER PUBLICATIONS

Mertens, Tom, et al., "Exposure Fusion", Pacific Graphics 2007, 9 pages.
(Continued)

*Primary Examiner* — Siamak Harandi
(74) *Attorney, Agent, or Firm* — Winstead PC

(57) ABSTRACT

An imaging system for generating images of biological samples having a surface, the system comprising: a sample support for supporting a biological sample in use; a plurality of illumination sources, the plurality of illumination sources being arranged around the sample support and each adapted to illuminate the biological sample, in use, from a different direction; an image capture device for capturing illumination which has impinged on the biological sample to thereby
(Continued)

form an image of the sample; wherein at least one of the illumination sources direction is not perpendicular to the surface of the sample.

13 Claims, 31 Drawing Sheets

(51) Int. Cl.
    *G01N 21/25*     (2006.01)
    *G01N 21/17*     (2006.01)
    *G01N 21/27*     (2006.01)

(52) U.S. Cl.
    CPC .... *G06T 7/0012* (2013.01); *G01N 2201/0626* (2013.01)

(56) References Cited

U.S. PATENT DOCUMENTS

| | | | |
|---|---|---|---|
| 7,186,990 | B2 | 3/2007 | Powers et al. |
| 2004/0101951 | A1 | 5/2004 | Vent et al. |
| 2004/0101954 | A1 | 5/2004 | Graessle et al. |
| 2010/0232660 | A1 | 9/2010 | Graessle et al. |
| 2011/0002525 | A1* | 1/2011 | Mimura ............... C12M 23/48 |
| | | | 382/133 |

FOREIGN PATENT DOCUMENTS

| | | |
|---|---|---|
| CN | 101650299 A | 2/2010 |
| EP | 2497823 A1 | 9/2012 |
| FR | 2786498 A1 | 6/2000 |
| FR | 2926820 A1 | 7/2009 |
| JP | 2010104301 A | 5/2010 |
| WO | WO-2010014244 A2 | 2/2010 |
| WO | WO-2011055791 A1 | 5/2011 |

OTHER PUBLICATIONS

Duda, Richard O, et al., "Use of the Hough Transformation to Detect Lines and Curves in Pictures", Graphics and Image Processing, Communications of the ACM, vol. 15, No. 1, Jan. 1972, pp. 11-15.

Canny, John, "A Computational Approach to Edge Detection", IEEE Transactions on Pattern Analysis and Machine Intelligence, vol. Pami-8, No. 6, Nov. 1986. pp. 679-698.

Boltz, Sylvain, "International Search Report," prepared for PCT/EP2012/058398, as mailed Jun. 5, 2012, 4 pages.

Huisken, J., et al., "Even Fluorescence Excitation by Multidirectional Selective Plane Illumination Microscopy (mSPIM)," Optics Letters, vol. 32, No. 17, Sep. 1, 2007, pp. 2608-2610.

Huisken, et al., "Selective Plane Illumination Microscopy Techniques in Developmental Biology," Development, vol. 136, No. 12, May 22, 2009, pp. 1963-1975.

* cited by examiner

| View | Opaque culture | Transparent / semi transparent culture |
|---|---|---|
| Backlight | If media is blood agar (COS / CAN / PVX / ....) show hemolysis | Better view of the information of the bottom of the dish (including serigraphy, bare codes, ....) |
| Near horizontal | N.A. | After correction, less impact of dish bottom on global view (less dust, less impact of serigraphy, ....) |
| Annular | Best view for over all color rendering. Closest to what biologist are used to see | |
| Lateral annular | Still good color rendering. Lighting from one side produces shadows that give some relief impression (some texture info), but non homogeneous colors | |
| Inverted annular | Other color rendering (same that could be obtained when changing light incidence on the dish) texture / relief impression with color information. Good view for swarming detection | |
| Vertical | Surface of the dish information. Good view for swarming detection, bubble, dust evidence. Monochrome information of colonies surface / aspect | |

Fig. 7

Differences between COS and CPS versions

| Modules / views used | V1 CPS | V1 COS |
|---|---|---|
| Number of views used | 4 : Backlight, Bottom, Left/Bottom, Top | 3 : Backlight, Bottom, Vertical |
| Isolated colonies detection | Backlight, Bottom, Top | Backlight, Bottom |
| Isolated colonies detection on serigraphy zone | Bottom, | Bottom, |
| Binarization | Backlight, Bottom, Left/Bottom | Bottom |
| Serigraphy detection | Backlight | Backlight |
| Positioning mark detection | Bottom | Bottom |
| Swarming detection | X | Vertical |
| Results visualisation | Bottom | Bottom |

Fig. 8

Objective

Source

Edge Lighting Correction $$\frac{1}{49}\begin{vmatrix} 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \\ 1 & 1 & 1 & 1 & 1 & 1 & 1 \end{vmatrix}$$

*Fig. 22*

IMAGING METHOD AND SYSTEM FOR ANALYZING IN-VITRO BIOLOGICAL SAMPLES

FIELD OF THE INVENTION

The present invention relates to a method and system for analyzing in vitro samples.

BACKGROUND OF THE INVENTION

In vitro analysis is carried out in many environments in order to identify biological samples such as microorganisms, cell and tissue cultures, cellular or sub-cellular extracts, and purified molecules. Samples of various materials are isolated from their usual biological context and provided with an environment in which they can grow. This environment is often provided in the form of a Petri dish which is placed into an incubator in order for the samples to grow. The Petri dish normally includes a microbiological culture medium which encourages growth of the sample. Ideally, incubation on an appropriate culture medium gives rise to the growth of a number of colonies of the sample. Subsequent analysis of the colonies is generally carried out to identify the microorganisms and assess their sensitivity or resistance to antimicrobials.

An important part of the analysis of the samples is the ability to identify particular microorganisms or bacteria, for example, from the colonies. In addition, the treatment of bacteria with appropriate medication can also be analyzed based on the growth of the microorganisms in the sample and the interaction with any medication applied to the sample.

Much of the preliminary analysis is carried out by visual analysis of the Petri dish by qualified scientists. The preliminary visual analysis works well, but is prone to human error and inconsistency due to the huge diversity of shapes, colors, sizes and forms of the different microorganisms which may be difficult to interpret. However, the visual domain is still one of the best ways to quickly identify microorganisms at present. In addition, as much of the growth is "random", it is not easy to model microorganism growth and find automated systems which lend themselves to the diversity identified above.

Known incubators may include a window through which samples can be viewed, but in general, the Petri dish is taken out of the incubator to be visually analyzed. The preliminary visual analysis involves holding the Petri dish in front of a light source to identify colonies. Further detailed chemical and microscope analysis methods can then be carried out on particular identified colonies, as required.

Biological scanners, i.e. devices used to scan or count bacterial colonies, are known in the state of the art. For example, US 2004/0101951 and US 2010/0232660 both disclose biological scanners for scanning biological growth plates having different structures but both having in common the ability to generate images of the plates and perform an analysis of these images to detect biological growth. However both use a single light source providing front or back illumination. Indeed, it is stated in both US2004/0101951 and US2010/0232660 that "some biological growth plates may require only front or back illumination, but not both." Such illumination is basic and does not allow images that have sufficient quality to carry out a preliminary analysis in an efficient manner to be obtained.

Certain prior art systems exist in which a sample in a Petri dish is illuminated by different colors or wavelengths of light in order to form images of the sample. The images are captured by an appropriately orientated camera.

FR2926820 discloses a method for detecting at least one specific microorganism in a biological sample, said method comprising, amongst others, the step of subjecting a culture medium to at least two radiations each presenting a specific wavelength.

Preferably, two lighting systems are used, each lighting system emitting radiation of a specific wavelength. More specifically, FIG. 1 of this document shows the combination of top visible lighting and ultraviolet backlighting. The subsequent combined image from the two different illuminations is then used to detect the presence of specific microorganisms.

Similarly, published Japanese patent application, JP2010104301, describes, amongst others, a method for detecting microorganisms comprising an imaging step to image a culture medium on which microorganisms grow and a colony detection step, said method also using combination of top lighting and backlighting.

Having acquired an image of a biological sample there are often processes which can be applied to enhance the image and carry out image processing. However, there are many problems associated with enhancing images of biological samples. These include:
  the sizes of colonies being viewed;
  the proximity of one colony to another;
  the color mix of the colonies;
  the nature of the Petri dish;
  the nature of the culture medium
  etc.
Many of these problems can only be solved by bespoke applications.

OBJECTS OF THE INVENTION

It is an object of the present invention to overcome at least some of the problems associated with the prior art.

It is a further object of the present invention to provide an automated system and method for analyzing biological samples.

SUMMARY OF THE INVENTION

The present invention provides a method and system as set out in the accompanying claims.

According to one aspect of the present invention there is provided an imaging system for generating images of biological samples having a surface, the system comprising a sample support for supporting a biological sample in use; a plurality of illumination sources, the plurality of illumination sources being arranged around the sample support and each adapted to illuminate the biological sample, in use, from a different direction; an image capture device for capturing illumination which has impinged on the biological sample to thereby form an image of the sample;
wherein at least one of the illumination sources direction is not perpendicular to the surface of the sample.

Optionally, the directions of at least two of the illumination sources are substantially not coplanar. In one embodiment, the largest angle of intersection between the directions of the at least two illumination sources is less than 170°, optionally less than 160°, optionally less than 150°. Using at least two illumination sources whose respective directions are substantially not coplanar allows improved identification and detection of objects, marks and characteristics of the objects.

Optionally, the plurality of illumination sources includes two or more of: a backlighting source; a near horizontal source; an annular source directed towards the surface; an annular source directed away from the surface; and a vertical source, wherein each defines a distinct type of illumination source.

Optionally, the at least two of the plurality of the illumination sources are of different types of illumination source.

Optionally, the plurality of illumination sources includes three or more of: a backlighting source; a near horizontal source; an annular source directed towards the surface; an annular source directed away from the surface; and a vertical source, wherein each defines a distinct type of illumination source.

Optionally, the at least three of the plurality of the illumination sources are of different types of illumination source.

Using at least two or three illumination sources of different types (such as a backlighting source, a near horizontal source, etc.) also allows improved identification and detection of objects, marks and characteristics of the objects.

Optionally, a plurality of illumination sources are used to produce a plurality of images, which can be combined to form a composite resultant image.

Optionally, different combinations of the plurality of illumination sources can be used to produce different images for different biological analyses.

Optionally, each illumination source is included in a unit and wherein each unit can be stacked one on top of another.

Optionally, the units are moveable relative to one another.

Optionally, the sample is movable relative to the plurality of illumination sources.

Optionally, the illumination sources comprise red, green, blue sources, white light sources or UV sources.

Optionally, the sample is capable of being illuminated by a near horizontal source.

Optionally, the system further comprises a processing system for enhancing or processing images to effect a biological analysis of the sample.

Optionally the system is combined with an incubator system for incubating samples prior to imaging the samples.

The invention also relates to an incubator for incubating biological samples including an imaging system as defined in the claims.

According to a further aspect of the present invention there is provided a method of generating images of biological samples wherein the sample has a surface, the method comprising the steps of:
illuminating a sample with a plurality of illumination sources, the plurality of illumination sources being arranged around the sample support and each being adapted to illuminate the biological sample, in use, from a different direction;
capturing illumination which has impinged on the biological sample to thereby form an image of the sample;
wherein the step of illuminating comprises illuminating the sample with at least one of the illumination sources which is directed in a direction which is not perpendicular to the surface of the sample.

According to a further aspect of the present invention there is provided a system and method for enhancing an image of a biological sample, which biological sample has been grown in a vessel on a culture medium and wherein the image has been formed by illuminating the vessel containing the sample and the culture medium with a near horizontal illumination beam, the method comprising the steps of obtaining an image of the vessel and the culture medium as a test image by applying separately a plurality of different colored illumination sources to the vessel and culture medium; for each color measuring the absorption of the vessel and the culture medium; forming a model of absorption of each color for the vessel and the culture medium; obtaining and processing an image of the vessel, culture medium and biological sample by applying separately the plurality of different colored illumination sources to the vessel, culture medium and biological sample; for each color generating a source image of the vessel, the culture medium and the biological sample; applying the model of absorption of each color for the vessel and the culture medium to the respective source image to remove the absorption effects of the vessel and the culture medium; combining the source images for each color to form a composite image highlighting the biological sample.

Optionally, the step of illuminating includes illuminating with a red, green, blue source and/or a UV source.

According to a further aspect of the present invention there is provided a system and method of determining an ideal exposure time for an image of a biological sample in a biological imaging system, the steps comprising identifying one or more characteristics of the sample to be imaged; determining a default exposure time based on the one or more characteristics; taking an image at the default exposure time; analyzing the image to determine a plurality of zones in the image, such as a zone relating to a field of interest and a zone which does not relate to the field of interest; determining a relative luminosity between the plurality of zones to estimate an expected luminosity of the image; in one of the zones, such as the zone relating to the sample, applying a classification algorithm to cluster together parts of the image relating to the biological sample and parts of the image which do not relate to the biological sample; determining the luminosity in each part to obtain a value for the actual luminosity of the image; comparing the actual and expected luminosities to determine a difference coefficient there between; if the coefficient is above a predetermined level deciding that the default exposure time was incorrect and then retaking a new image at a new exposure time based on the coefficient.

According to a further aspect of the present invention there is provided a system and method of determining the contours and relief information on a surface of a biological sample, from an image thereof, the method comprising the steps of illuminating a sample with at least one vertical source above the sample and obtaining a monochrome image of the sample; illuminating the sample with a second source from any direction to produce a second image of the sample; applying a transform to the monochrome image to form a transformed monochrome image; suppressing low frequency luminance values in the transformed monochrome image; determining a luminance value of each pixel in the transformed monochrome image; combining the luminance values with the second image on a pixel by pixel basis to form a final image which accentuates the contours and provides relief information.

Optionally, the step of illuminating the sample with at least one vertical source above the sample and obtaining a monochrome image of the sample comprises illuminating the sample with at least two vertical sources at at least two different positions.

Optionally, the step of illuminating the sample with the second source comprises using a source having a plurality of color channels and forming the second image as a color image.

Optionally, the step of illuminating the sample with the second source comprises illuminating the sample with each of a red, green and blue source separately and combining the luminance values with each of the resultant red, green and blue images to form an image which accentuates the contours and provides relief information for each color and combining the three colors to obtain said final image. Optionally, the sample is a Petri dish including a culture medium on which microorganism colonies are present.

According to a further aspect of the present invention there is provided a system and method of detecting characteristics associated with a vessel comprising the steps of obtaining one or more images of the vessel using one or more of a plurality of illumination sources, each illumination source capable of illuminating the vessel from a different direction; applying a object detection transformation to identify edges of the vessel; determining the image of the interior of the vessel.

Optionally the step of determining the image of the interior of the vessel comprises masking the edges of the vessel from the or each image to produce a resultant image showing the interior of the vessel.

Optionally the method further comprises identifying the absence of any microorganism colonies within the vessel.

According to a further aspect of the present invention there is provided a system and method of detecting objects of a predetermined format having non-biological characteristics on a vessel comprising the steps of obtaining one or more images of the vessel using one or more of a plurality of illumination sources, each illumination source capable of illuminating the vessel from a different direction; forming a digital image of the or each image; identifying objects of the predetermined format having non-biological characteristics.

Optionally the step of forming a digital image of the or each image comprises retrieving objects having a point shape and a dark color in the one or more images of the vessel.

Optionally the method further comprises masking the identified objects to produce a resultant image in which the objects are not visible.

According to a further aspect of the present invention there is provided a system and method of isolating microorganism colonies in a vessel including a culture medium, the method comprising the steps of obtaining one or more images of the vessel using one or more of a plurality of illumination sources, each illumination source capable of illuminating the vessel from a different direction; selecting an image or combination of images for further processing; applying a circular object detection transformation to identify one or more substantially circular objects in the vessel, which circular objects are representative of isolated colonies in the vessel; for each identified substantially circular object, determining an area of isolation for that object.

Optionally the step of determining the area of isolation of an object comprises determining the centre of the identified substantially circular object; forming a digitized image of the identified substantially circular object by applying a binarization step to obtain a binarized image, wherein the centre of the binarized image corresponds to the centre of the identified substantially circular object; verifying the circularity of the object in the binarized image; carrying out a test to identify the area of isolation of the object to determine the size of the colony and the area of isolation of that colony from other colonies.

According to a further aspect of the present invention there is provided a system and method of detecting a mass of colonies and/or non-circular colonies in a vessel including a culture medium, the method comprising the steps of obtaining one or more images of the vessel using one or more of a plurality of illumination sources, each illumination source capable of illuminating the vessel from a different direction; forming a digitized image of the images; detecting growth by identifying high density of colonies and non-circular colonies.

Optionally the step of identifying high density of colonies and non-circular colonies comprises determining areas having a contrast above a predetermined value.

Optionally the step of forming a digitized image of the images comprises segmenting the images with a region-based segmentation technique.

According to a further aspect of the present invention there is provided a system and method of detecting swarming microorganisms in a vessel including a culture medium, the method comprising the steps of obtaining one or more images of the vessel using one or more of a plurality of illumination sources, each illumination source capable of illuminating the vessel from a different direction; selecting an image having contour or relief information; applying a predetermined filter to the selected image to form a filtered image; subtracting the selected image from the filtered image to produce an image showing texture.

Optionally, the step of applying a filter comprises applying a median 7×7 filter to each point in the digitized image.

According to a further aspect of the present invention there is provided a system and method of detecting $\alpha$ and/or $\beta$ hemolysis performed by at least one microorganism in a vessel including a culture medium, the method comprising the steps of:
   obtaining first and second images of the vessel using one or more of a plurality of illumination sources, each illumination source capable of illuminating the vessel from a different direction;
   combining first and second images based on an fusion algorithm to apply different weights to different image characteristics to produce a color image having contour information making it possible to detect $\alpha$ and/or $\beta$ hemolysis.

BRIEF DESCRIPTION OF THE DRAWINGS

Reference will now be made, by way of example, to the accompanying drawings, in which:

FIG. 7 is a table showing different illumination types for different applications, according to one aspect of the present invention;

FIG. 8 is a table showing different illumination types for different culture media associated with different image processing techniques, according to one aspect of the present invention;

FIG. 22 is a matrix for use in an image processing technique, according to one aspect of the present invention;

DETAILED DESCRIPTION OF THE PREFERRED EMBODIMENTS

The present invention relates to a system for analyzing biological specimens in a fully or semi automated manner. In the present description, the term 'object' relates to a real object such as bubbles or colonies, the term 'mark' relates to a characteristic of a vessel such as an artifact or a serigraphy, and the term 'feature' relates to a characteristic of an object. In addition, the term 'Petri plate' defines an assembly of a Petri dish and a lid to cover the Petri dish.

Figure 1:
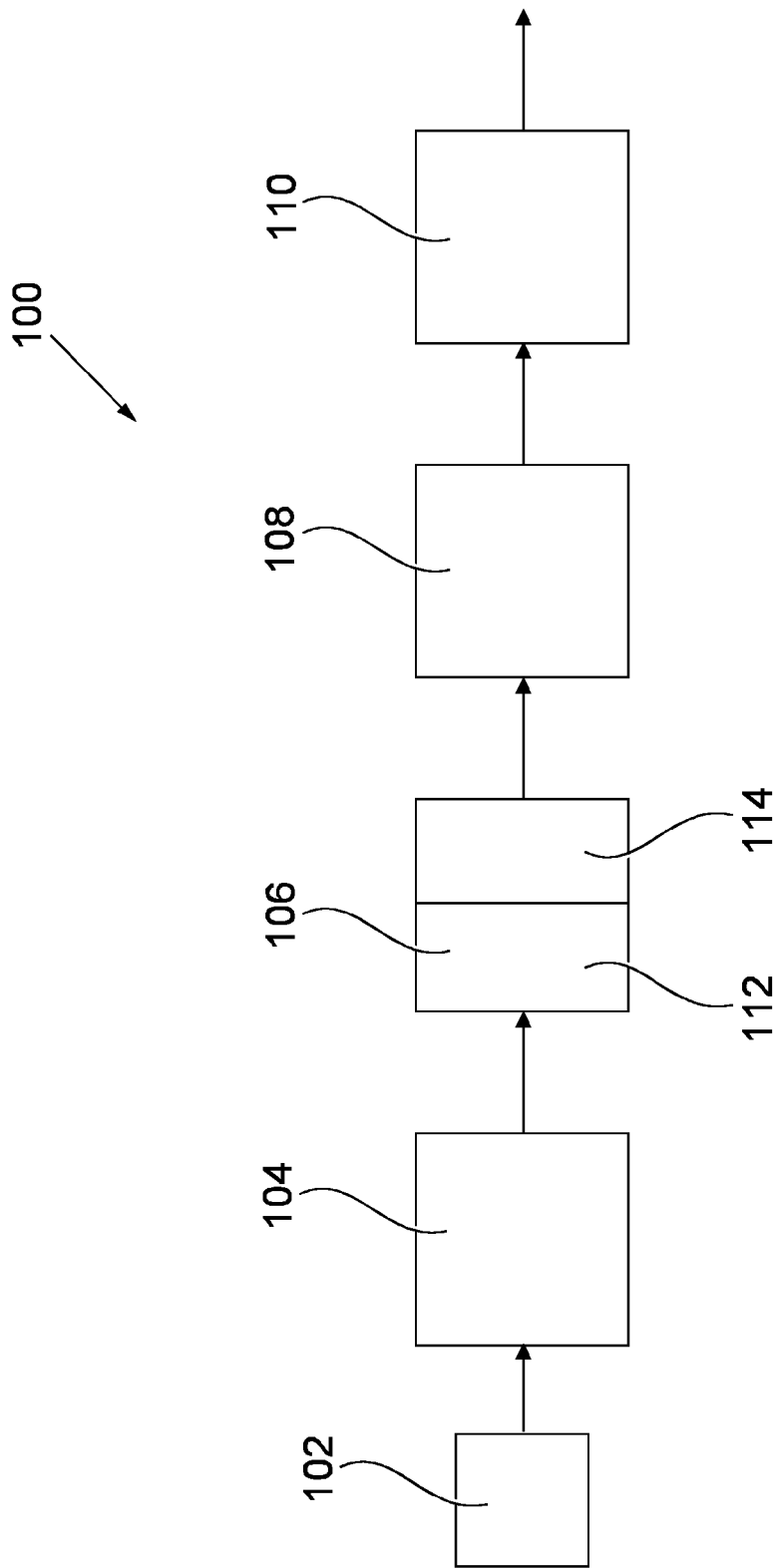
FIG. 1 is a biological analysis system, according to one aspect of the present invention.

FIG. 1 shows an example of a system 100 according to the present invention.

The system 100 includes a sample vessel bank 102, an automatic streaking machine 104, a smart incubator system 106, a processing unit 108 and an identification system 110.

The sample bank 102 produces manually or automatically sample vessels into which biological samples can be grown and analyzed. The sample vessel is typically a Petri dish, although other vessels may also be used. Accordingly, reference to a Petri dish herein is not intended to be limitative.

The sample vessel bank adds an appropriate culture medium to the dish to enable the biological sample to grow. The Petri dish may be passed from the sample vessel bank to the following stage of the process by means of a conveyor belt or other automated system. Alternatively, the samples can be passed by an operator.

The automatic streaking machine 104 applies a biological sample to the Petri dish and then distributes the sample in a known manner. For example, in a Petri dish the sample is applied using a comb having a length approximately equal to the radius of the dish. The comb is applied and then turned to spread the biological sample over the surface of the dish. An example of a suitable automatic streaking machine is commercialized by the applicant under the PREVI® Isola brand name.

Once the biological sample has been distributed over the culture medium in the dish, the dish is passed to the next stage of the process manually by an operator or by means of a conveyor belt or other automated system.

The smart incubator system 106 includes an incubator 112 and an imaging system 114. The Petri dish is introduced into the incubator and is incubated for a predetermined time at a predetermined temperature. This causes the biological sample to grow producing a number of colonies of microorganisms over the surface of the dish. Once the dish has been incubated as required, the dish is passed to the imaging system 114. The imaging system is a unique, novel system for generating images of the colonies and cultures generated in the system as a whole. The details of the imaging system will be described further below.

The images are used in the first stage of analysis of the samples. This stage can identify colonies and other aspects of the biological sample to aid and facilitate further activities and functions of the overall system.

After the images of the dish have been produced, the dish is then passed to the next stage of the process. This may be carried out automatically by a conveyor belt or other automated system or by an operator.

The processing unit 108 can take on a variety of different forms depending on the required sample analysis. For example, particular colonies may be extracted, based on the images, for further analysis or processing. Many other processes can be applied to the dish at this time. If necessary, the dish can be returned to the incubator for further growth and/or returned to the imaging system.

After all the necessary processing and imaging has been completed, the dish may be passed to the identification system 110 by means of a manual or automated process. The identification system 110 may be used to identify the microorganisms that are present in the form of colonies on the dish, in a multitude of different ways. Identification can be carried out by the analysis of the metabolism of the microorganism and can be automated or manual. An automated analysis can be carried out for example, with a VITEK® system commercialized by the applicant. The identification can also be performed using mass spectrometry technology. Other analysis could also comprise detecting antimicrobial resistance mechanisms.

It will be appreciated that the various elements of the overall system may be changed to carry out different functions. In addition, certain steps may be carried out in different orders.

Figure 2C:
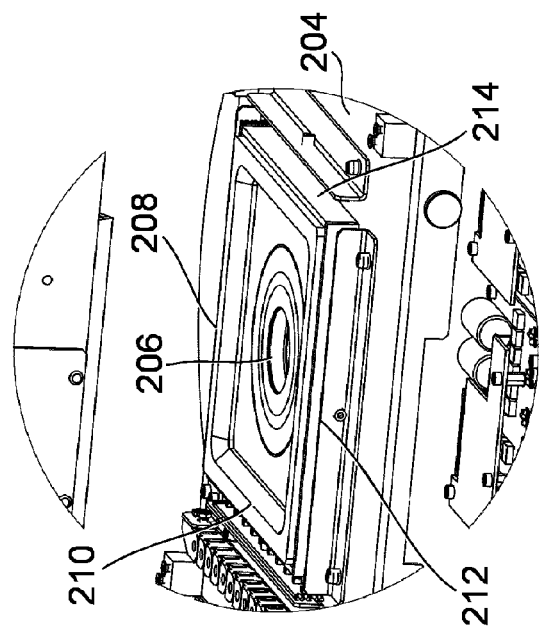
FIGS. 2a, 2b and 2c are schematic diagrams of the imaging system of the FIG. 1 system, according to one aspect of the present invention.
Figure 2A:
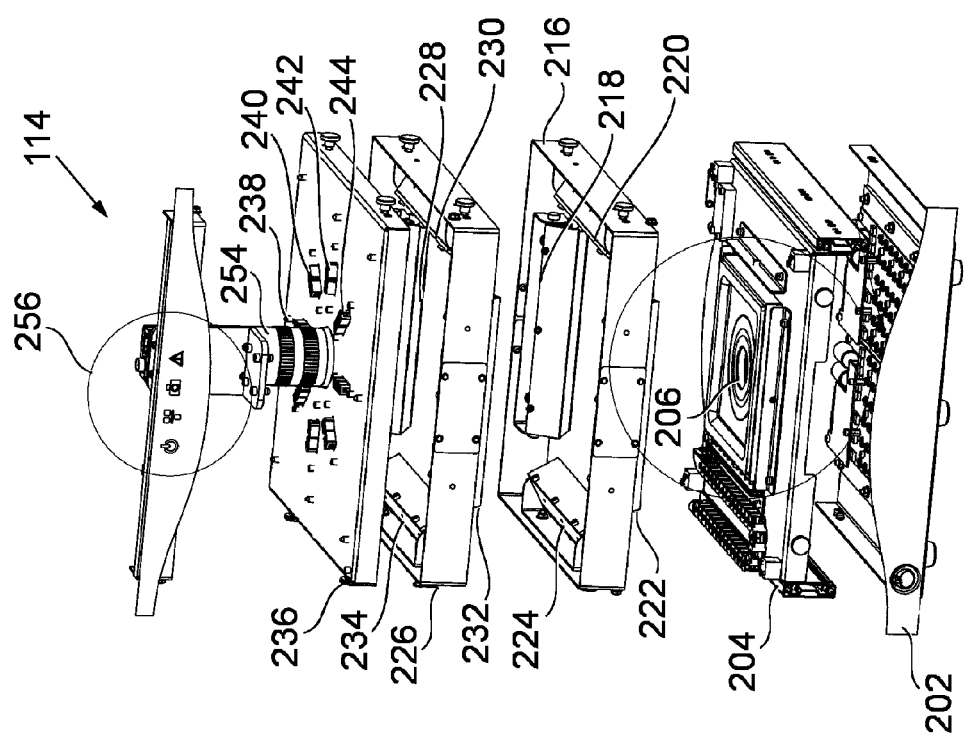
Figure 2B:
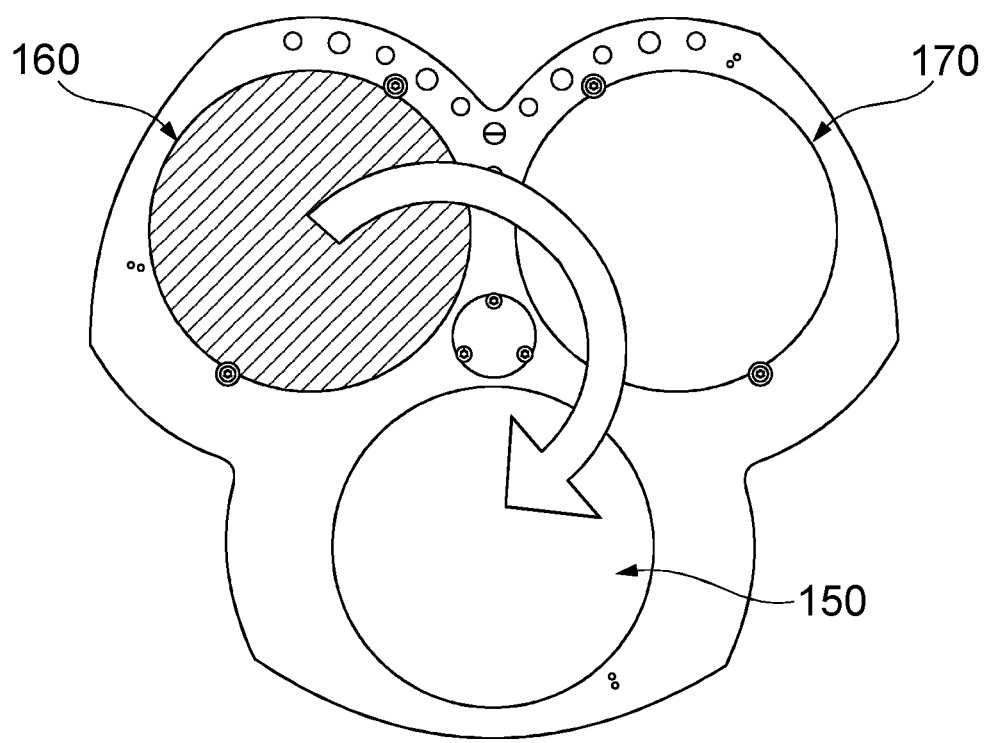

As previously mentioned the smart incubator system is an important aspect of the present invention and includes the unique imaging system. The imaging system will now be described in greater detail with reference to FIGS. 2a, 2b and 2c. The imaging system 114 includes a base unit 202. The base unit includes the optics and control circuitry for generating red, green and blue backlighting illumination. The base unit may include a controller which may be in the form of a wheel that has three positions as shown in FIG. 2b. These positions correspond to different illuminations which are "noBackground", "whiteBackground" and "blackBackground". The "noBackground" position relates to a circular hole 150 in the wheel. The "whiteBackground" position relates to a white background circle 160 in the wheel. The "blackBackground" position relates to a black background circle 170 in the wheel. No background is used for backlight, whilst white and black are used for all other types of illumination, depending on the nature of the sample.

Above the base unit, there is a sample holding unit 204. The sample holding unit may include a drawer which can slide in and out and includes a recess 206 which is adapted to support a Petri dish. In addition, as shown in FIG. 2c, the sample holding unit includes four red, green, blue horizontal illumination sources, respectively 208, 210, 212 and 214. The four illumination sources are located rectilinearly around the sample recess and are independently controllable. In use, the top of the Petri dish is substantially in line with the top of the four horizontal illumination sources. The horizontal illumination sources allow the Petri dish to be illuminated with a horizontal or near horizontal beam.

It should be noted that the bottom of the recess is optically transmissive to allow the backlight illumination to illuminate the sample in use. The sample holding unit further includes the optics and controls required to operate the four horizontal illumination sources.

The sample holding unit may comprise an alternative orientation (not shown) in which the samples are passed into position for imaging by a conveyor belt. The drawer may be replaced by a conveyor belt system having sample holding zones, each of which is transparent to allow backlighting to be used. The conveyor belt system can move the sample into an appropriate position and then the necessary images can be taken. The conveyor belt then moves the next sample into position for imaging and the first sample on to the next stage of processing. This enables images to be taken at different positions and when the sample is moving.

In a further alternative, the system may include a robotic arm which is able to load Petri dishes into the sample holder or on to the conveyor belt. In addition, the robotic arm may remove the lid of the Petri dish prior to imaging and replace the lid there after. This can be done by inverting the Petri dish and causing the lid to fall off. Removing the lid ensures the lid does not produce reflections when the sample is illuminated by certain illumination sources.

Figure 24:
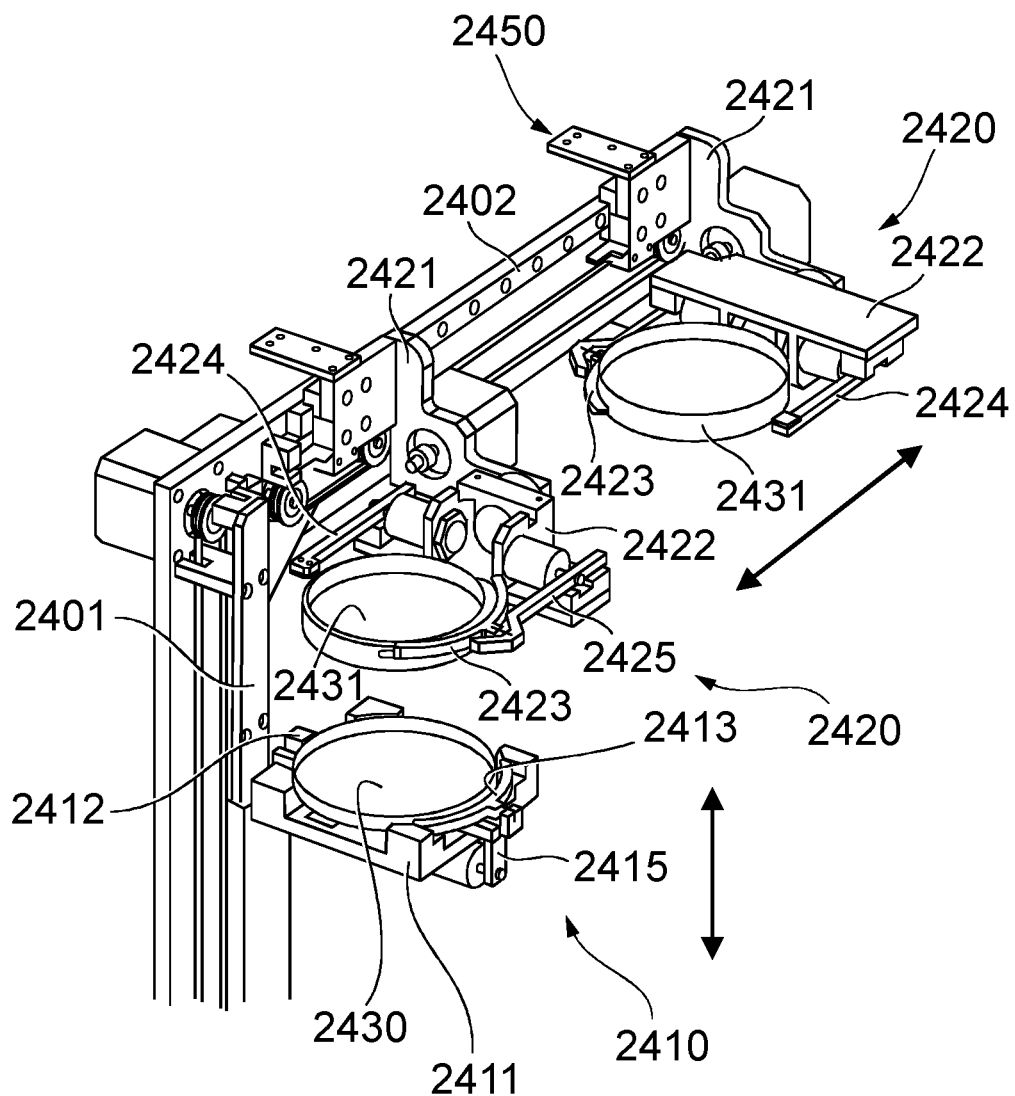
FIGS. 24 and 25 are a schematic representation of a robotic arm of the imaging system, according to one aspect of the present invention.
Figure 25:
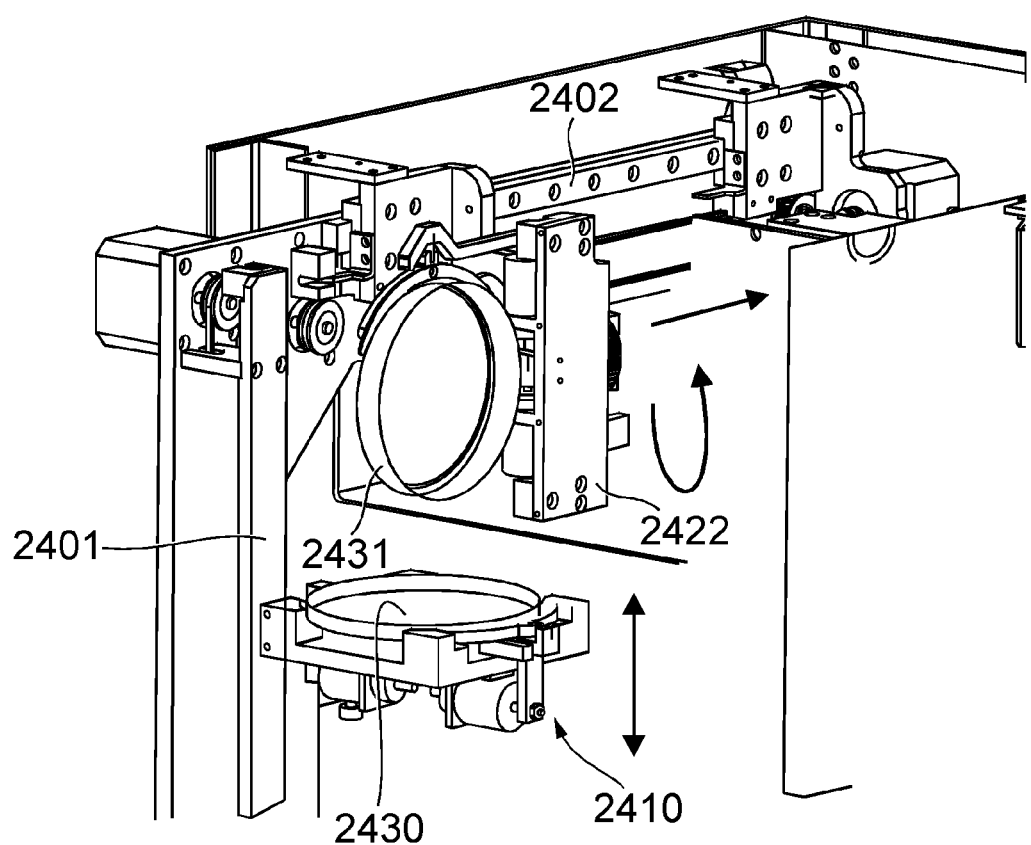

A possible embodiment of the robotic arm is shown in FIGS. 24 and 25 as described below.

In addition, to movement into and out of the imaging zone the sample holding unit may also include a mechanism to change the position of the sample relative to the normal position. For example the sample holder may be able to orientate the sample to be at a specific angle to a specific beam. Other movements, for example rotation, of the sample can also be carried out with appropriate mechanisms. As a result any relative movement of the sample and the illumination sources can be realized by moving either the sample in the sample holding unit or the illumination source. The variations are endless.

Figure 26:
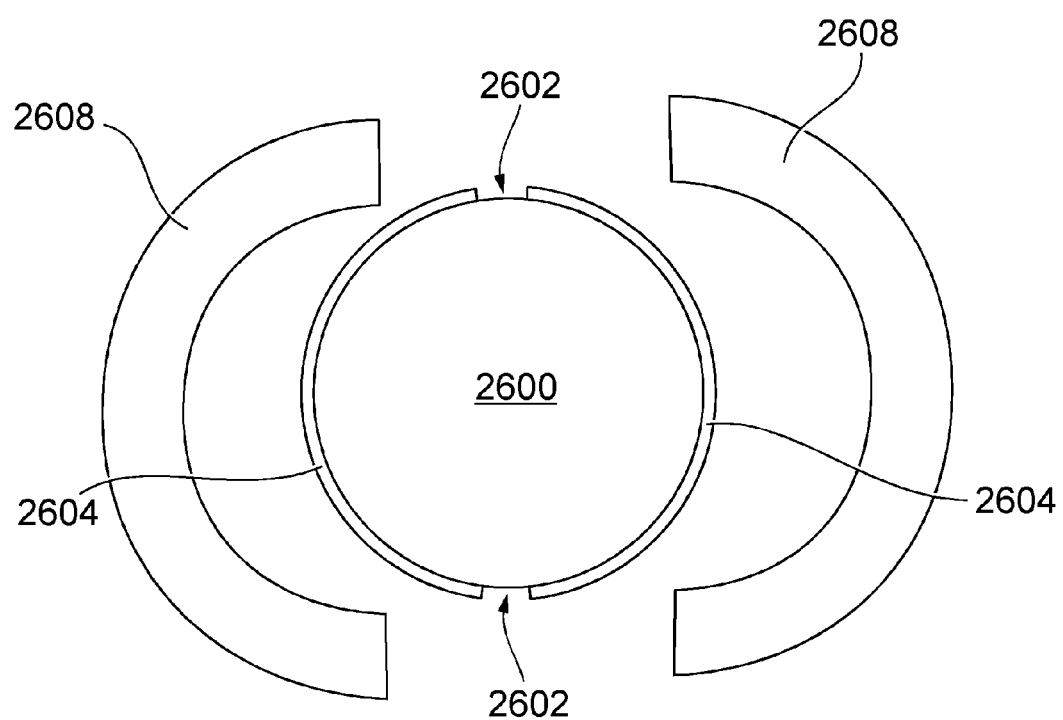
FIG. 26 is a schematic representation of a mask for the Petri dish, according to one aspect of the present invention.

In the situation where the sample holding unit has a normal position such as a horizontal position over the wheel in the imaging system, a mask may be added to improve the quality of images taken of the interior of the Petri dish. An embodiment related to the Petri dish provided with a mask is shown in FIG. 26 as described below.

The imaging system 114 further includes a first intermediate unit 216 which is situated above the sample holding unit. The first intermediate unit includes four rectilinearly positioned red, green, blue illumination sources 218, 220, 222 and 224 respectively. The illumination sources are adapted, in use, to produce annular illumination onto the sample recess in the sample holding unit and are each independently controllable. The annular illumination can be adjusted to be incident on the sample from any appropriate direction, including lateral, non-lateral or any other appropriate orientation.

The imaging system also includes a second intermediate unit 226. The second intermediate unit includes four rectilinearly positioned red, green, blue illumination sources 228, 230, 232 and 234 respectively. The illumination sources are directed upwards and reflect from the unit above to give rise to an inverse annular illumination which, in use, illuminates the sample in the sample recess and are each independently controllable.

A head unit 236 of the imaging system is located above the second intermediate unit. The head unit includes white light illumination sources, of which four are shown, respectively 238, 240, 242, 244, 246, 248, 250 and 252 which are each independently controllable. The eight illumination sources are arranged, in use, to produce vertical illumination onto the sample recess.

The head unit also includes an image capture device 254, such as a camera which is directed towards the sample recess. Illumination from any combination of illumination sources from any of the units can be directed to the sample recess. The image capture device can then capture images from any samples in the sample recess which have been illuminated. The use and further processing of the images will be explained in greater detail below.

The head unit may also include a control pad 256 which is used to operate the various light sources. In addition to the control circuitry and optics in each unit which controls the function thereof, there may be an overall control system (not shown). The control system may include a computer, a display unit, processing modules and image enhancing algorithms, image processing, and any other processes or techniques.

The control system may be used to control which illumination sources are used for specific applications. In addition, the control system may apply difference image enhancing techniques and image processing for different applications. Image enhancing techniques are methods and techniques to enhance the quality of the image or to make pertinent information visible for an expert to view. Examples, that will be described in greater detail below include: fusion of different images such as vertical fusion or fusion for hemolysis, edge lighting correction, exposure time correction etc. Image processing is the extraction of information from images in order to provide decision support or automatic decisions. This does not necessarily include a modification of the image but instead a determination of higher level information/interpretation in an automated manner Examples, that will be described in greater detail below include: detection of the dish ring, detection of marks, detection of growth (masses, isolated colonies, swarming), global decision on growth/no growth, etc.

Swarming is intended to indicate swarming motility, which is a rapid (2-10 µm/s) and coordinated translocation of a bacterial population across solid or semi-solid surfaces. This type of motility has been mostly studied in genus *Serratia, Salmonella, Aeromonas, Bacillus, Yersinia, Pseudomonas, Proteus, Vibrio* and *Escherichia*.

The control system may be used to carry out any other function and/or control operation for the imaging system. These include, but are not limited to,
  loading and unloading the sample into the sample recess;
  checking and adjusting the positioning of the sample in the sample recess;
  controlling the level of luminance;
  controlling the balance of the red, green, blue components;
  controlling exposure time;
  controlling illumination combinations;
  testing the system;
  calibrating the system; and
  any other appropriate control based on the use and purpose of the analysis.

Each of the units forming the imaging system are capable of being moved relative to the other units. When this occurs, certain optical adjustments may be necessary to ensure the sample is illuminated by all sources.

The operation of the imaging system will now be described in more detail with reference to FIG. 3.

Figure 3:
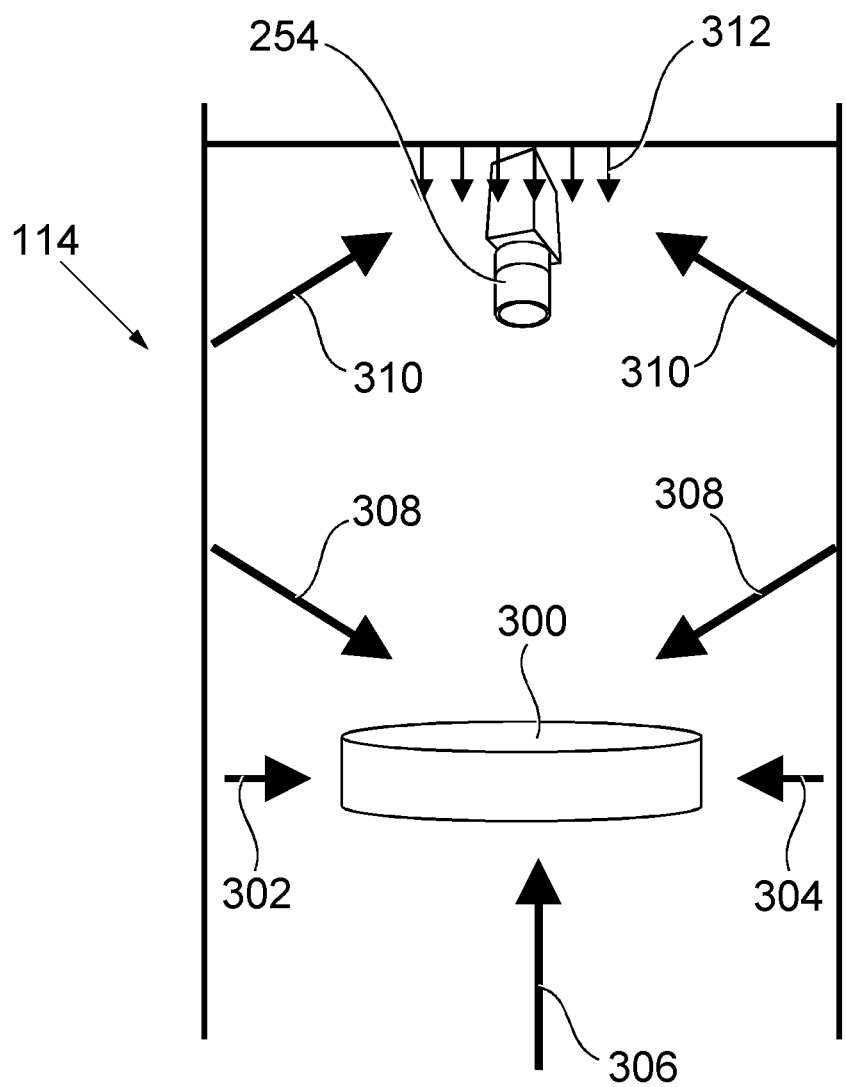
FIG. 3 is a simplified diagram of the FIG. 2 system showing the different types of illumination applied to a sample, according to one aspect of the present invention.

FIG. 3 shows a schematic diagram of the imaging system 114 to demonstrate the various illumination sources and how they impact on a sample 300 located in the imaging system. The sample 300 may be illuminated by a near horizontal beam 302, 304. The near horizontal beam in fact includes components into and out of the paper in addition to those illustrated by references 302 and 304. The near horizontal beam is produced by the horizontal illumination sources in the sample holding unit 204 of FIG. 2. The sample may also be illuminated by a backlight beam 306 generated by the base unit 202 in FIG. 2.

An annular beam 308 may also illuminate the sample 300 and is produced by the first intermediate unit 216. An inverse annular beam 310 produced by the second intermediate unit 226 can also illuminate the sample.

A vertical beam 312 can also illuminate the sample and is generated by the illumination sources in the head unit 236.

The vertical beam and the backlight illumination apply illumination in a substantially perpendicular direction relative to the sample in the Petri dish. The optical axis of each of these illuminations sources is accordingly also perpendicular to the sample. The near horizontal, the annular and inverse annular illuminations are not perpendicular to the Petri dish. Similarly therefore the optical axes of these sources are non-perpendicular to the sample. The non-perpendicular sources provide a diverse range or alternative images to those achieved with perpendicular sources. These non-perpendicular sources provide additional and different optical feature in any image created with them. This ensures that isolation and detection of colonies is improved.

Figure 4A:
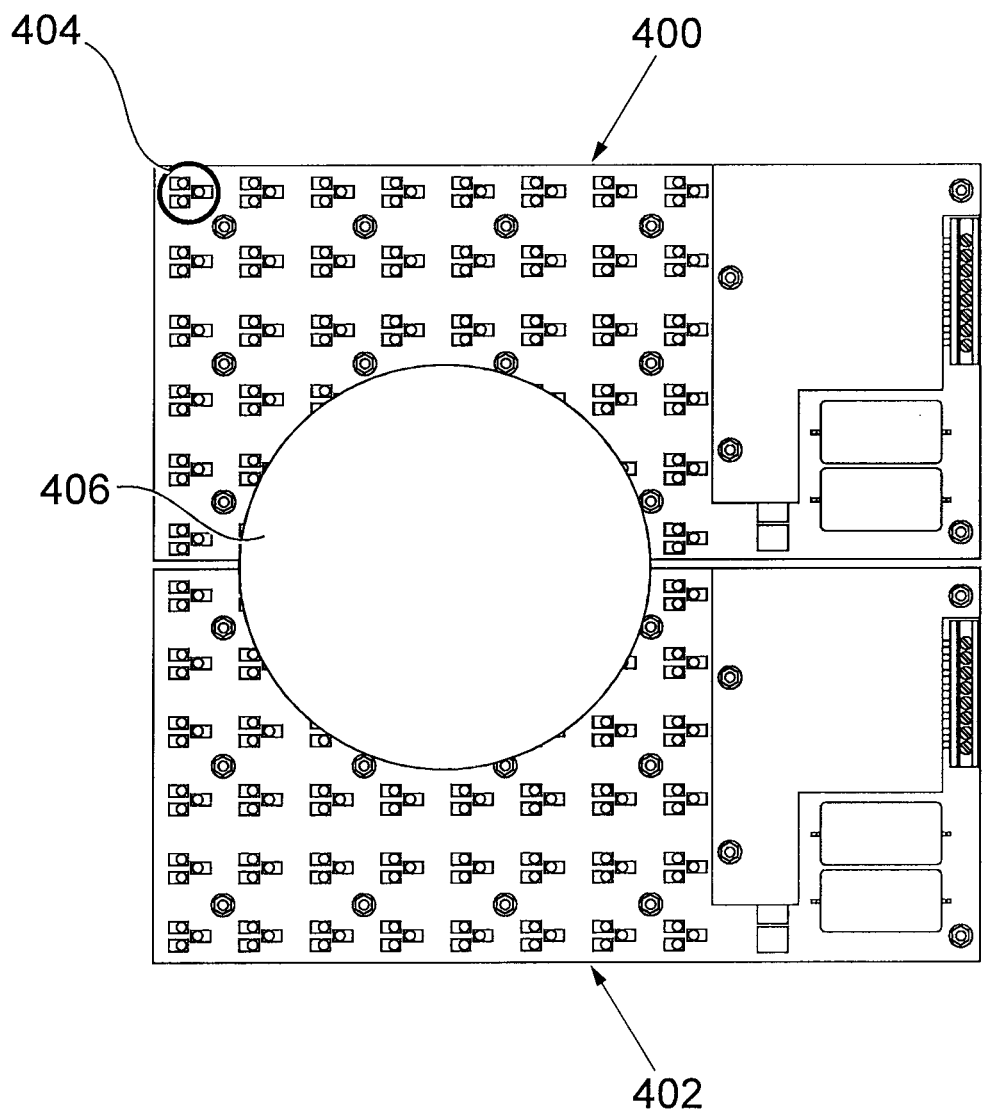
FIG. 4a is a schematic representation of the backlight illumination source, according to one aspect of the present invention.

The illumination sources shown in FIG. 3 and produced by the appropriate unit in FIG. 2 may be of any preferred type, such as light emitting diodes (LED) operating at red, green and blue (RGB) frequencies; a simple white light source; an ultra-violet (UV) source or any other appropriate radiation source. The illumination sources may comprise for example 322 LEDs including 64 white LEDs, 86 red LEDs, 86 green LEDs and 86 blue LEDs. The number of light sources in any location can vary from that shown and described herein. RGB illumination is provided at each location by a trio of three LEDs operating at each respective frequency. For different illumination sources there may be different combinations of RGB LEDs. For example, for the backlight illumination the LEDs may be orientated as shown in FIG. 4a. Each type of illumination is provided by means of specific cards comprising specific arrangements of LEDs. The base unit 202 produces the backlight beam 306 by means of two cards 400 and 402 each including a plurality of diodes arranged in threes. Each trio of LEDs 404 includes a red, green and blue LED. The position of the sample is shown at 406. In total, 45 trios of LED are located on each card and are used to generate the backlight beam 306. Among each trio, the red, green and blue LEDs can be illuminated one at a time to produce one colored illumination after the other.

It will be appreciated that any appropriate orientation and number of diodes can be used instead of the example described above. In addition, different combinations of RGB can be selected and used.

In addition, for UV sources, the UV illumination is provided by means of two cards which are simultaneously lighted. Each card comprises a UV LED of 500 mA intensity, for example.

Figure 4B:
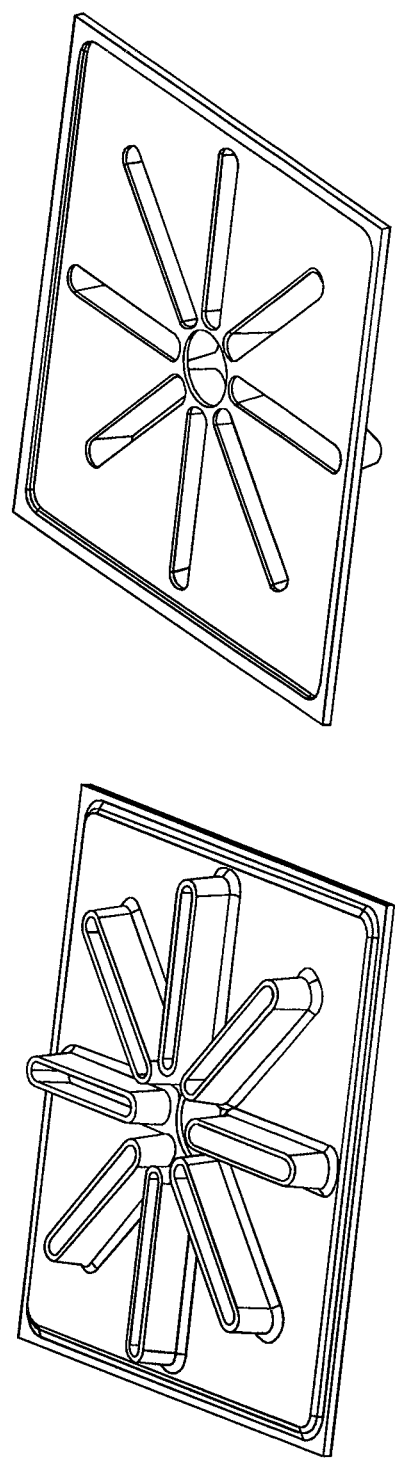
FIG. 4b is a schematic front view and rear view representation of a diffuser related to a backlight illumination.

The card may include sensors for determining temperature and possible aberrations of the LEDs, so that the LEDs can be switched off for a few seconds in continuous operation if problems can be foreseen. As shown in FIG. 4b, there may also be a diffuser between the card 400, 402 and the sample in the recess. The diffuser helps to prevent the LEDs being visible in the resulting picture and also helps to make the background light homogenous. In addition, the diffuser absorbs some of the illumination from the powerful LEDs. When direct lighting was used a very short exposure time may be used to minimize any effects relating to so called smearing caused by the camera.

Figure 5:
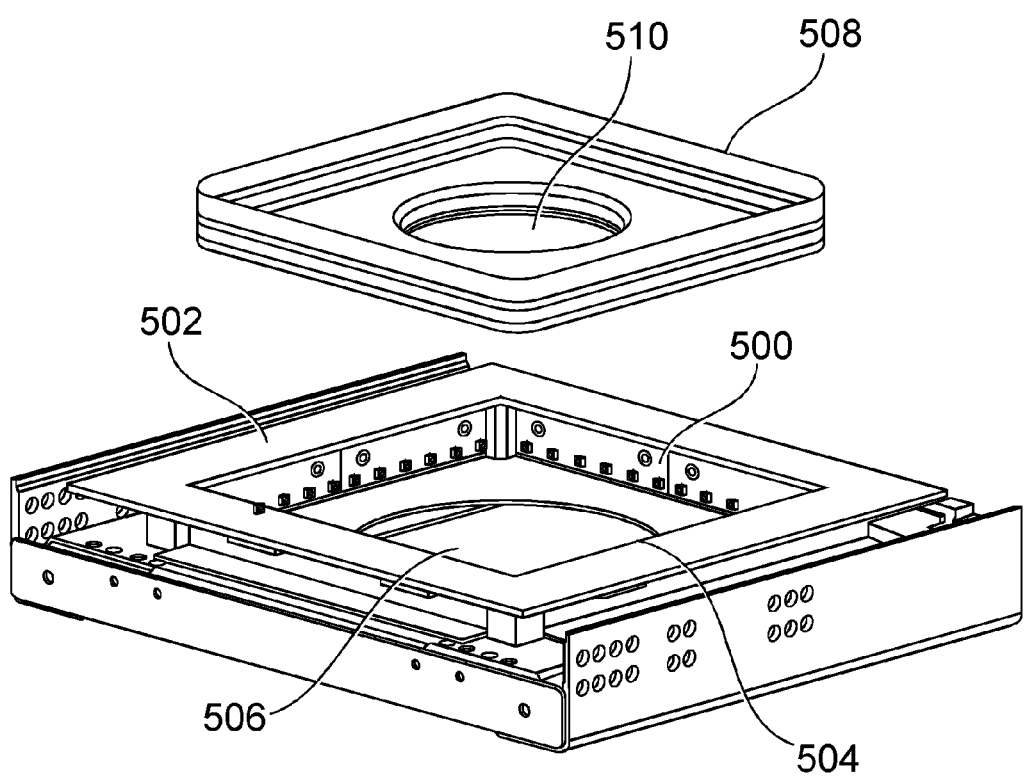
FIG. 5 is a schematic representation of the sample drawer and associated near horizontal illumination source, according to one aspect of the present invention.

FIG. 5 shows the illumination sources located in the sample holding unit 204 producing the near horizontal beam 302, 304. There are eight cards, each covering half the length of a side, 500, 502, 504 and 506 respectively. Each card carries an array of 8 trios of RGB LEDs. The illumination sources can be controlled together independently or in any predetermined sequence. The eight cards form part of the sample drawer mechanism which includes the sample recess. An optically transmissive interface 508 can be used having different sized apertures 510 for different sized samples or Petri dishes.

Figure 4C:
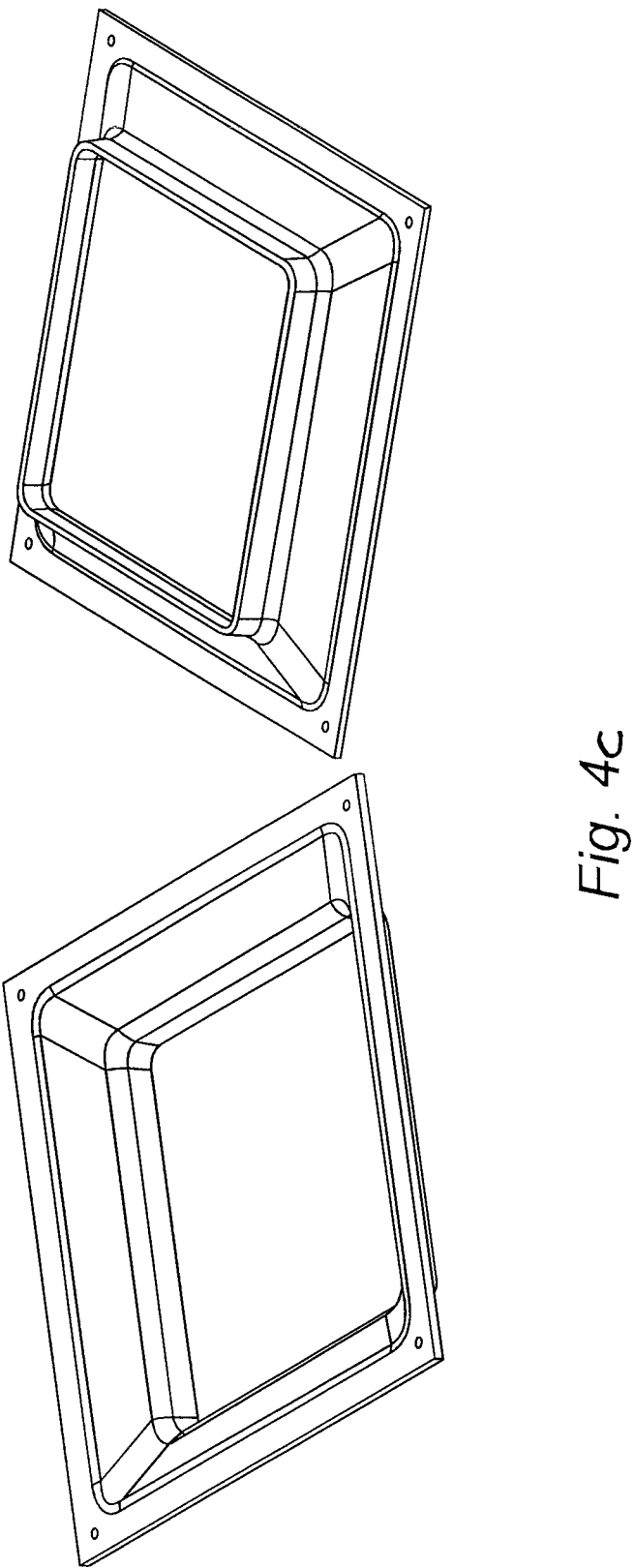
FIG. 4c is a schematic front view and rear view representation of a diffuser related to annular illumination.
Figure 6:
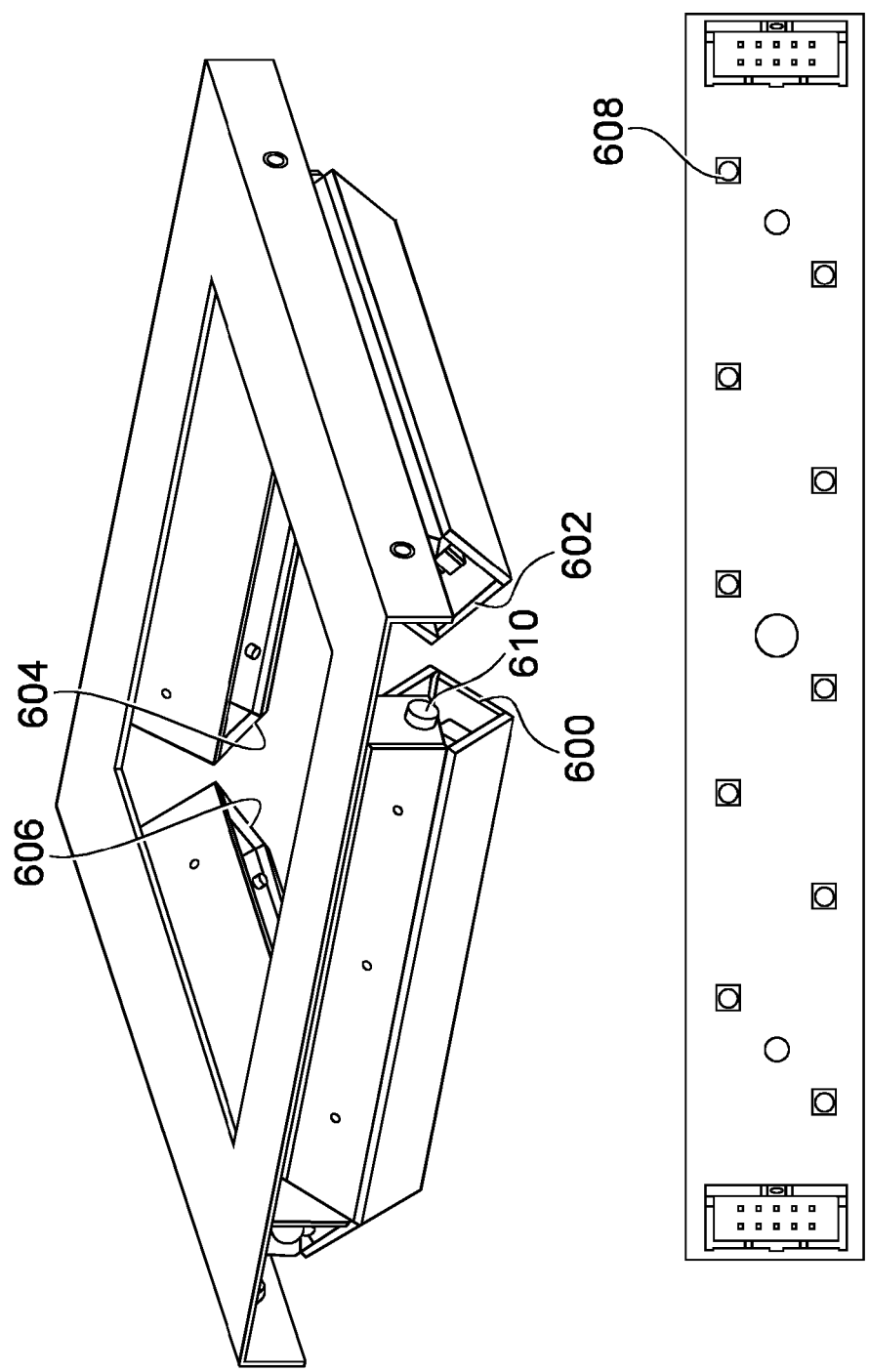
FIG. 6 is a schematic representation of the annular illumination source, according to one aspect of the present invention.

Referring to FIG. 6, each of the four illumination sources in the first and second intermediate units 216 and 226 respectively include four cards 600, 602, 604 and 606 respectively each having an array of 10 RGB LEDs 608 oriented as shown. These arrays give rise to the annular beam 308 in the case of the first intermediate unit 216 and the inverse annular beam 310 in the case of the second intermediate unit 226. Each card can be controlled independently such that each card can be controlled either together or separately. To prevent unwanted reflection from the sample and the culture medium each card is equipped with a diffuser as shown in FIG. 4c. Each of the cards can be rotated about an axis (one of which is shown as 610) such that the annular beam can be positioned to optimize illumination of the sample. This adjustment is necessary to ensure homogeneous illumination irrespective of the vertical position of the intermediate units relative to the sample.

FIG. 6 shows the positions of the cards for the first intermediate unit 216. It will be appreciated that those for the second intermediate unit 226 will be directed upwards and rotation will be adjusted accordingly.

The vertical illumination sources 238, 240, 242, 244, 246, 248, 250 and 252, in the head unit 236, each comprise a white light source where each source is independently controllable to produce the vertical beam 312.

The image capture device 254 is adapted to capture images of the sample from above. For a Petri dish having a 90 mm diameter an image 100 mm$^2$ will be produced. This typically equates to 2050 pixels$^2$ in a standard image capture device, although other pixel sizes may also be used, for example 2448×2050 pixels. In addition, since the dish is generally of the order of 13 mm in height, the depth of field of the imaging device is between ±6 mm depending on the height of the culture medium layer in the Petri dish.

In all instances of the illumination mentioned above the image of the sample is captured from above by the imaging devices 254. It should be noted that the camera may take a sequential set of images over a predetermined time period to measure the growth of colonies and other time related effects. In addition, the camera may be a video camera for certain applications where growth progress of colonies, and the like, is being measured. Movement of the dish may also be brought about by movement of the dish into and out of the imaging system by means of a suitable conveyor belt or robotic arm.

The camera is adapted to take different types of images from different illumination sources. Typically a sequence of images is taken for a specific application. The sequence comprises the steps of illuminating the sample with a specific illumination or combinations of illumination, followed by taking a specific type of image, such as monochrome, black and white, RGB with the relevant illumination. Then a next image is taken with a different type of illumination or combination thereof and the sequence continues until all the required images have been taken. The camera is controlled within the sequence to take the appropriate type of image.

The camera may for example comprise a monochromic sensor and use the progressive scan CCD technology with a maximal speed of 17 images per second. The camera may have a power consumption of 12 to 24 Volts DC.

More details of the images produced and the image enhancement processes will now be described.

As previously mentioned, a sample in the imaging system 114 can be illuminated from a plurality of different light sources, which strike the sample from different directions. After the sample has been illuminated an image of the sample is taken from above. Each illumination highlights different aspects of the sample.

The backlight illumination shows detail of the Petri dish including any markings on the base thereof, the form of the edge and the lid of the Petri dish; and a detailed view of the layout and density of the colonies in the sample. This illumination provides information which can isolate colonies, determine the difference between similar colonies (for example α and β hemolytic species) and generally gives a view of the contents of the sample.

The near horizontal illumination is refracted and reflected by the sample and the contents thereof to form an image which can be used to isolate and eliminate artifacts. In addition, this image can be used to make corrections based on the absorption of illumination by the culture medium as will be described in further detail below. The image may also be used later to determine the percentage cover of the dish by colonies to provide an estimate of colony concentration and to determine growth or no growth on non opaque culture media.

The annular illumination is directed towards the sample and is reflected or refracted to the image capture device by the culture medium and any colonies which have been formed. The purpose of the image produced by this illumination is the ability to distinguish the colors of the culture medium and the colonies. The ability to identify color is often an important tool for identifying specific microorganisms as some have very distinctive coloration. The overall result is a view which is the closest to what a biologist would expect to see for a specific type of microorganism, for example, colors, colony aspects, etc. This is particularly important to identify the subtle changes in coloration in the medium and around the colonies. In addition, images produced by annular illumination allow detection of subtle variations of colors below and around the bacterial colonies in chromogenic media.

The lateral annular illumination is an illumination of only one of the sources 218, 220, 222 and 224. This gives an image having shadows which can be used to identify contours and relief. Each of the sources will give rise to different shadow effects as a result of the direction of illumination.

The inverse annular illumination is reflected from the head unit onto the sample. The sample then reflects or refracts the illumination to the image capture device. The image thus captured gives details of the contrast of the different colonies in the sample. This image can also contribute color information. In addition, this image can provide texture information; aspect and color of the colonies; information on swarming limits and certain information about the relief of the colonies, such as elevation, form and shape.

The inverse annular illumination produces a quasi-vertical illumination which enables visualization of changes in gradient. This gives texture and granularity information and is useful in detecting colonies which do not have much elevation but have surface irregularities. In one embodiment, a number of different images are taking using the inverse annular illumination and subsequently combined in order to deal with the possibility of saturation of the image.

The vertical illumination source illuminates the sample from above. The illumination is reflected by the sample and colonies to give an image which provides detailed contour information. This can be used to identify the relief of the sample and the height of colonies. This information can then be used to identify specific types of microorganisms as the relief of a colony is often very specific. For example, certain colonies are dome shaped, others are bumpy, other are flat, etc.

As described above each of the illumination sources and directions can be used to accentuate and enhance different image characteristics. The examples described may be changed or adapted by using illumination from different sources and directions without departing from the scope of the present invention.

Furthermore, different wavelengths of illumination can be used for different applications, for example infra red and ultraviolet.

Another important application of the present invention is to create images from a combination of illumination sources to generate a composite image which can accentuate and enhance more than one characteristic of the image of the sample. For example, a combination of a backlight image and an annular image can be particularly useful in the recognition of certain characteristics or properties of similar colonies, such as α or β hemolysis.

Another factor which can have an effect on the image generated is the type of culture medium used to grow the sample. Many different culture media exist; these include CPS which is a culture medium particularly adapted to identify *E-coli, Proteus*, and KESC using a urine sample; and COS which is a culture medium including blood which is useful in identifying hemolytic ability.

Different culture media, such as CPS and COS are quite different in nature and color. As a result, illumination acting thereon may produce different types of image. As such different illumination sources and combinations of sources may be used for different culture media.

FIG. 7 is a table which identifies the various types of illumination as described above and a set of possible uses for those illuminations for certain applications. As previously mentioned there are many different types of culture medium. These can be broadly categorized as opaque or transparent/semitransparent culture media. The table indicates the potential uses of each of the different types of illumination for the different types of culture media. The table is self explanatory and shows some of the optimal light conditions for carrying out certain applications and analyses. The backlight is conveniently used to show hemolysis in opaque blood cultures and to give a better view of the information on the bottom of the dish in transparent or semitransparent cultures.

Near horizontal illumination is inappropriate for opaque cultures but is useful in transparent and semitransparent cultures to remove dish artifacts and reduce the impact of dust and Serigraphy.

The annular illumination provides the best view for color rendering to provide an image that is closest to that which the biologist is used to seeing. The lateral annular illumination also gives good color rendering and as the lighting comes from one side the production of shadows can give some relief impression and texture information, although this makes the color information less homogeneous.

The inverted annular illumination gives rise to further color rendering and also provides texture and relief impression with the color information. This is particularly useful in giving an accurate view of swarming.

The vertical illumination is useful to determine surface information and also gives a good view of swarming, detection of bubbles, dust etc. Monochrome information of the colony surfaces and aspect are readily produced.

The variety of direction of illumination provided by the present invention provides an advantage, as many different types of illumination can be used to obtain images of colonies grown in a sample. The different images can be used to identify different characteristics and as a result provide an improved way of identifying these characteristics.

In addition, image processing can be used on the images to produce enhanced images, which are still more useful when it comes to analyzing the colonies and other aspects of the sample. For example, the writing on the bottom of a Petri dish can be identified and automatically removed by means of appropriate algorithms. This gives rise to an image which is clear of the writing on the dish.

Other algorithms can be used to facilitate different image enhancement techniques. The following section will identify several examples of image enhancing algorithms which improve the image produced by the system.

One type of illumination used in the present invention is unique in the field of biological imaging. This is the near horizontal beam. Using a near horizontal beam on a Petri dish means that the beam passes through the edges of the Petri dish and lid and through the culture medium. This causes absorption of the light and would be expected to be less useful than beams from other directions in terms of identifying colonies and characteristics thereof. However, this is not the case.

Figure 9B:
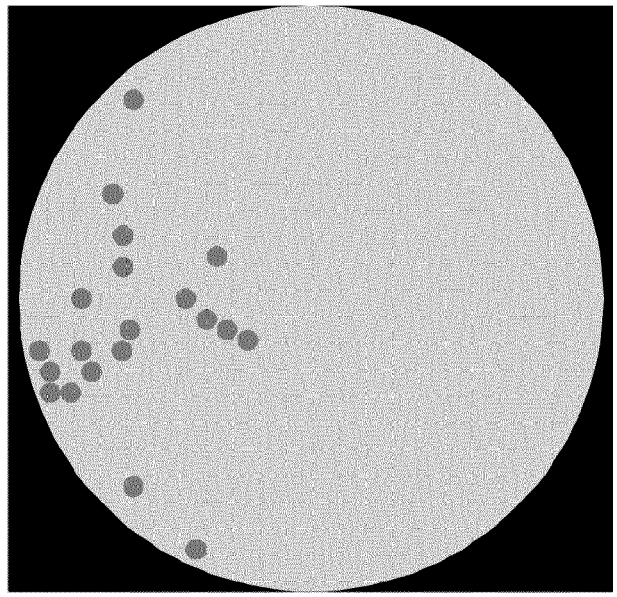
FIG. 9b is a resultant image after the first image enhancement technique, according to one aspect of the present invention.
Figure 9A:
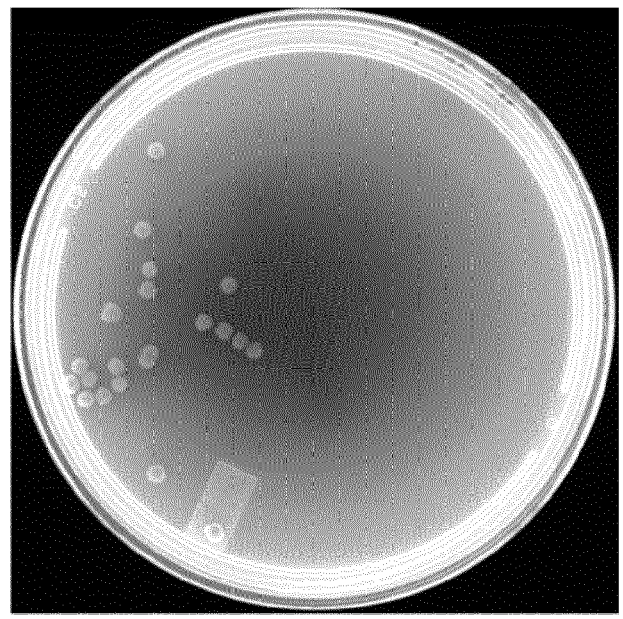
FIG. 9a is a source image for a first image enhancement technique, according to one aspect of the present invention.

The use of a near horizontal beam adds a significant amount of valuable information. This is the case even when there is significant absorption of the illumination as the beam passes through the Petri dish and culture medium. As the near horizontal beam collides with colonies, the beam is reflected and/or refracted towards the image capture device. This results in an image which clearly shows the positions of colonies. The result may be as shown in FIG. 9a. Whilst this image is useful it includes a number of optical effects which make colony identification non optimal. For example the culture medium may have a non-uniform surface which has changes in color and contrast across the sample. In addition, the edge includes significant interference based on the various layers of the Petri dish through which the illumination passes. This makes it difficult to identify colonies at the edge of the sample.

Accordingly, there is a need to improve the quality of this image to make it easier to identify colonies. The present invention proposes an edge lighting correction process to attempt to improve the quality and usefulness of this image.

Figure 10:
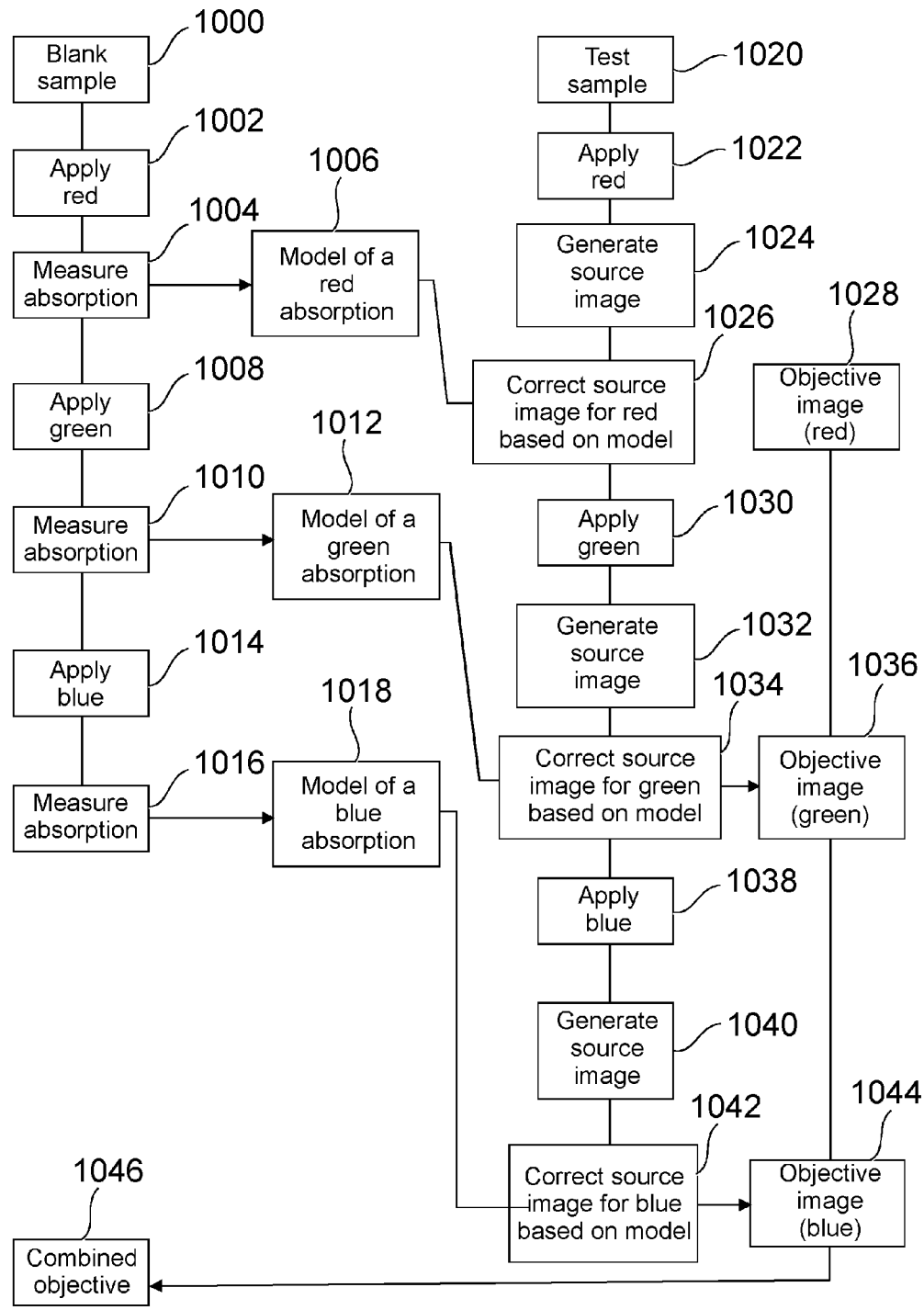
FIG. 10 is a flow chart showing the steps of a first image enhancement technique, according to one aspect of the present invention.

The edge lighting correction process will now be described with reference to FIG. 10. A blank sample is placed in the sample recess at step 1000. This blank sample is a Petri dish with culture medium but no colonies or other biological growth.

Figure 11C:
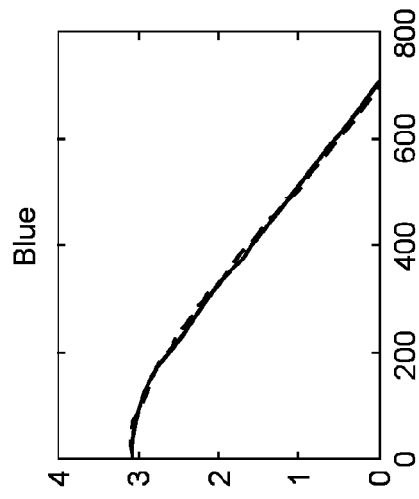
FIGS. 11a, 11b and 11c are graphs showing absorption measurements and models for red, green and blue, according to one aspect of the present invention.
Figure 11B:
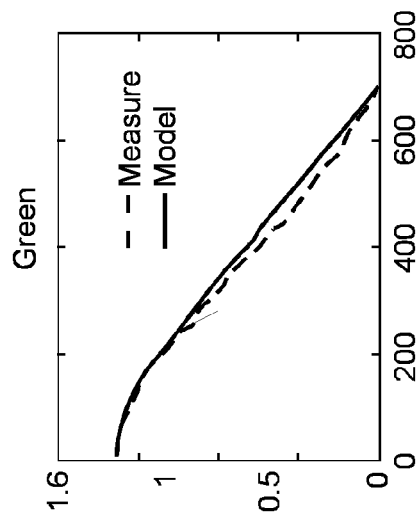
Figure 11A:
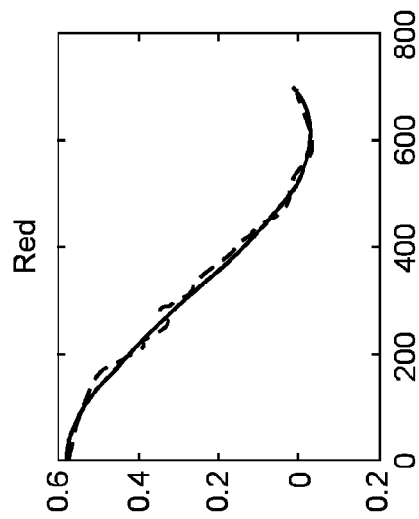

A near horizontal red illumination in step 1002 is applied to the blank sample and the red absorption is measured in step 1004. An example of measured red absorption is shown in FIG. 11a. The red absorption is then modeled and a model of red absorption is generated at step 1006. The red absorption model is also shown on FIG. 11a.

A near horizontal green illumination in step 1008 is applied to the blank sample and the green absorption is measured in step 1010. An example of measured green absorption is shown in FIG. 11b. The green absorption is then modeled and a model of green absorption is generated at step 1012. The green absorption model is also shown on FIG. 11b.

A near horizontal blue illumination in step 1014 is applied to the blank sample and the blue absorption is measured in step 1016. An example of measured blue absorption is shown in FIG. 11c. The blue absorption is then modeled and a model of blue absorption is generated at step 1018. The blue absorption model is also shown on FIG. 11c.

The models of red, green and blue absorption are stored in the system and referenced to a particular blank sample type. There may be many models for many different types of blank sample. The models are stored as separate red, green and blue models in this case, but could equally well be combined and stored as a RGB or white absorption model. The models could be empirical models, based on measurements as described above. Similarly, other types of models can be used, such as mathematical models or computer generated models. Such models are based on the combination of intrinsic absorption properties of compounds constituting the culture medium. Also, different models can be derived for different types of illumination. For example a model for UV illumination would be different for a model for RGB illumination.

Returning to FIG. 10, the test sample analysis to apply edge lighting correction is now described. The test sample is loaded into the sample recess at step 1020. The relevant blank sample is identified and the associated models are loaded into the system.

A near horizontal red beam is applied to the sample at step 1022. A source image (red) is then generated by the image capture device at step 1024. The red absorption model is used to correct the source image (red) for the red based model at step 1026. This is generally carried out by a differencing process or algorithm. An objective image (red) is then created at step 1028.

A near horizontal green beam is applied to the sample at step 1030. A source image (green) is then generated by the image capture device at step 1032. The green absorption model is used to correct the source image (green) for the green based model at step 1034. This is generally carried out by a differencing process or algorithm. An objective image (green) is then created at step 1036.

A near horizontal blue beam is applied to the sample at step 1038. A source image (blue) is then generated by the image capture device at step 1040. The blue absorption model is used to correct the source image (blue) for the blue based model at step 1042. This is generally carried out by a differencing process or algorithm. An objective image (blue) is then created at step 1044.

The three objective images are then combined into a combined objective image at step 1046. An example of the combined objective image is shown in FIG. 9b.

The edge lighting correction process has made the colonies more visible and well more defined. With this image it is very easy to isolate a specific colony and then carry out further analysis on this colony.

The use of a near horizontal beam with the edge lighting correction technique of the present invention offers significant advantages in the identification and isolation of colonies. The stark contrast between the source and objective images is very clear. A user would have a much greater chance of identifying colonies if using the edge lighting correction process of the present invention.

In another image enhancing technique, the exposure time of an image is considered and regulated, to optimize the exposure time. A reason for wanting to optimize the exposure time is to improve the visibility of colonies relative to the culture medium. It is a complex problem to determining the necessary exposure time for a Petri dish which is under analysis to identify microorganisms and colonies grown therein. The problem arises as a result of a number of specific attributes of this type of analysis.

Firstly the Petri dish contains a culture medium which can have different attributes in terms of transparency, opaqueness, darkness, lightness, etc. Another problem is the actual presence of the Petri dish itself, which can give rise to surface and edge reflections. If exposure conditions are non-optimal, it may be more difficult to distinguish between colonies and the culture medium in order to accurately determine the position of a colony in the Petri dish.

Figure 12:
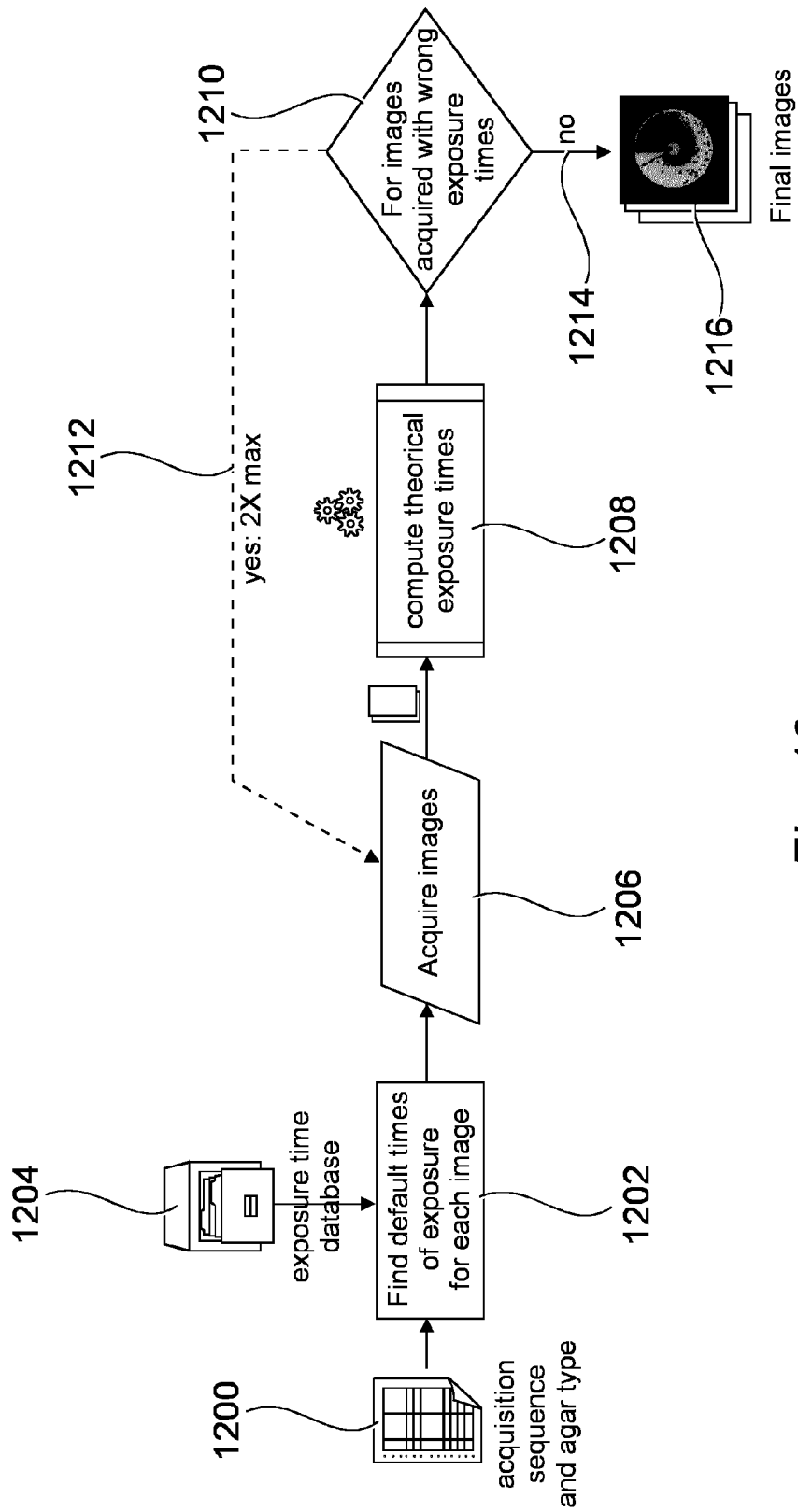
FIG. 12 is a flow chart of a further image enhancement technique, according to one aspect of the present invention.

FIG. 12 shows a flow chart of a process according to the present invention for acquiring an image having an optimal exposure time. In a first instance, at step 1200, an acquisition sequence and a culture medium type are identified. An acquisition sequence is a set of lighting, background light conditions, such as "noBackground", "whiteBackground" and "blackBackground"; and image capture parameters and orders which are repeated several times for the semi automated analysis. In addition, other information or characteristics may be taken into consideration. This includes characteristics relating to the source of illumination used to create the image; species type; concentration of species; etc. At step 1202 a default exposure time is determined for each image. The default exposure time may be a predetermined set time or may be based on historical data from an exposure time database 1204. The exposure time database may be populated with optimum exposure times for certain culture media, for a certain sample and/or for a certain combination of culture medium and sample. The database may include default times associated with any one characteristic or any combination of the known characteristics of the image. This information can be preloaded or produced by feedback from the process itself. As a result, once a characteristic is identified at step 1200, the corresponding default exposure time can be retrieved from the database 1204. The database may include a table indicating maximum and minimum exposure times for each of the specific illumination sources. This table may be used to determine a default exposure time if there is no default exposure already determined. Having established the default exposure time an image is acquired at step 1206. The default exposure time is selected to be T0. An RGB initial image may be obtained and transformed based on hue saturation values (HSV), if required by the camera. This occurs in the present invention but may not always be required.

The acquired image is then analyzed and a computation of optimum theoretical exposure time is made at step 1208 below. This analysis and computation will be described in further detail, with reference to the processing algorithm. At step 1210 a determination is made as to whether the default exposure time and the optimum theoretical exposure time are the same or not. If they are not substantially similar (1212) the process returns to step 1206 and a new image is acquired with a new exposure time T1, which is determined as described below. If at step 1210 the default and the theoretical exposure times are substantially similar (1214) the image is finalized at step 1216.

Figure 13:
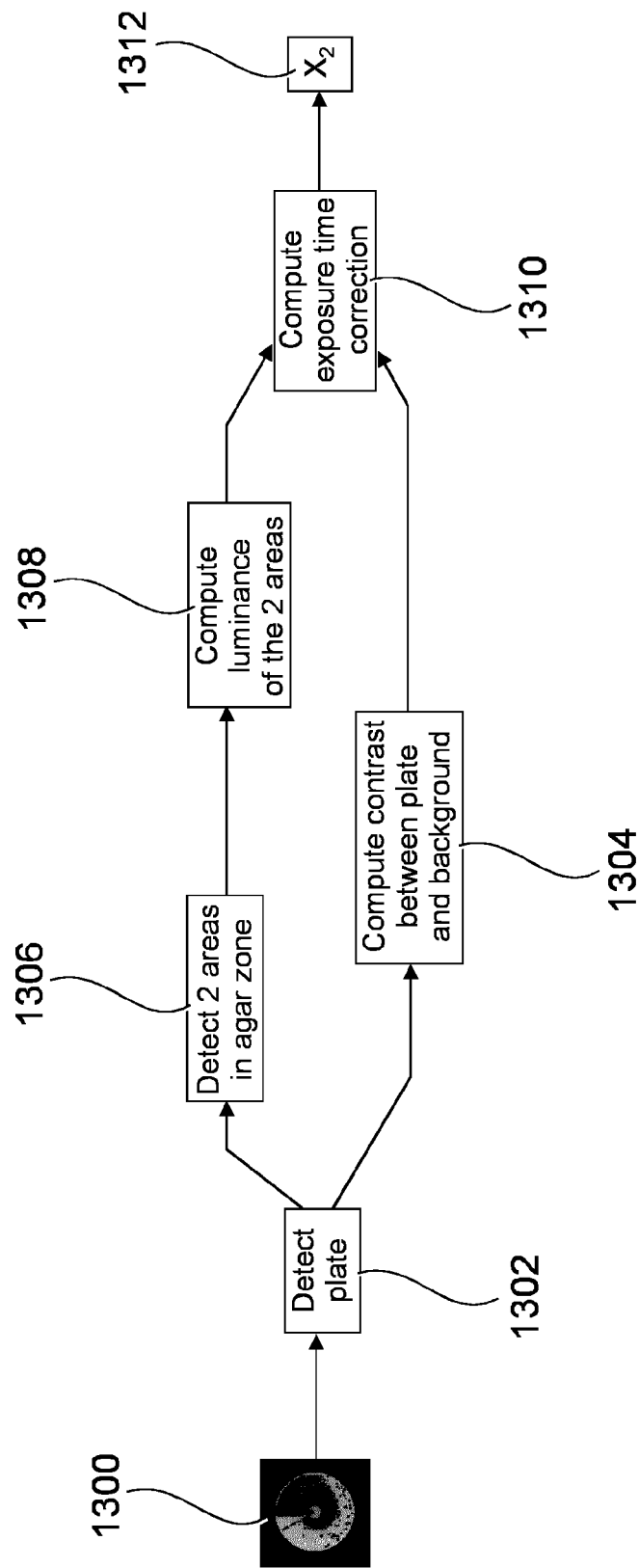
FIG. 13 is a flow chart of one of the elements of the FIG. 12 flow chart, according to one aspect of the present invention.

At step 1208 a computation is made which will now be described with reference to FIG. 13. The acquired image enters the process at step 1300. The contours of the dish are detected at step 1302. This allows the image to be split into two parts. These parts are those within the dish (i.e. in the field of interest) and those outside the dish (i.e. of no interest). This in turn enables a ring corresponding to the Petri dish walls to be isolated and then subsequently ignored.

In a step 1304 the contrast between the part outside the dish (Iout) and the part within the dish (Iin) is determined.

The contrast is measured as follows based on the luminosity inside and outside the dish, Lin and Lout respectively. The contrast can also have a dependency on the nature of the culture media, and whether the illumination has been reflected or transmitted. It should be noted that COS is a dark culture medium and reacts in different ways under reflection and transmission. The contrast (cp) is calculated from the luminosity of I1in and I1out (named Lin and Lout) as follows:

$$cp = \frac{Lin - Lout}{Lin + Lout}$$

The values determined here are then used to determine the expected Luminosity Lt in the final image in conjunction with other measurements, as described below in step 1310.

In the meantime the area within the dish is further processed at step 1306 in order to determine two areas within the field of interest. These two areas essentially relate to the areas in the dish where there are only culture media and the areas in the dish where colonies have grown. This is achieved by using a K-means clustering algorithm which attempts to form a cluster around a central mean for that cluster. Instead of a clustering algorithm other types of classification algorithm may alternatively be used. In the present invention the image has been converted to a hue, saturation value (HSV) and the algorithm is applied separately to the "saturated" components of the image and the "value" components of the image and the hue is initially ignored. For each application of the algorithm (one on the saturation component and one on the value component), two classes of pixels are determined by the K-means algorithm, the numbers of pixels in each class are named [Ns1, Ns2] and [Nv1, Nv2]. The following steps are then carried out.

In order to converge the algorithm the following steps are carried out:

If [min (Ns1, Ns2)>min (Nv1, Nv2) and min (Ns1, Ns2)>0] the classes are kept in the saturation image.

If [min (Ns1, Ns2)≤min (Nv1, Nv2) and min (Nv1, Nv2)>0] the classes are kept in the value image.

Figure 14:
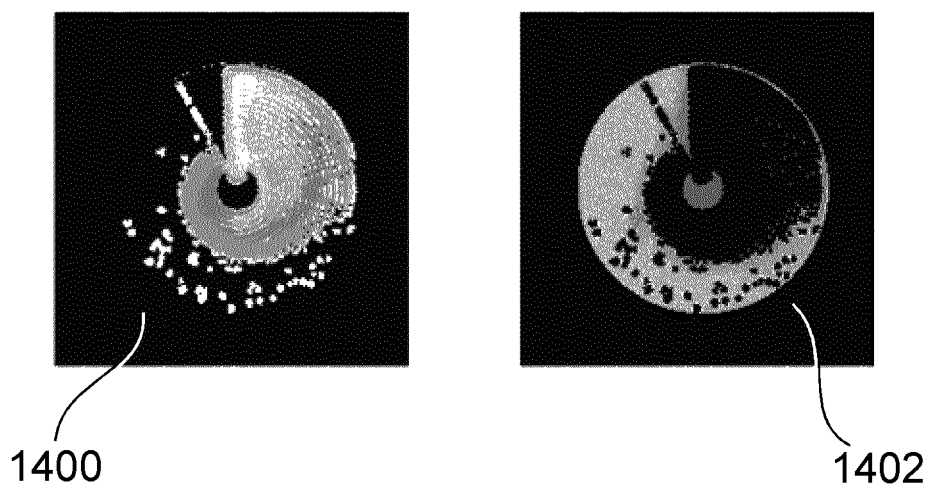
FIG. 14 is two resultant images after the further image enhancement technique, according to one aspect of the present invention.

If [min (Ns1, Ns2)=min (Nv1, Nv2)=0] as the algorithm has not converged, the K-means algorithm is reapplied on the hue layer and pixel classes considered on this layer. Finally, according to the pixel classes determined by the clustering algorithm, two complementary images Iin1 and Iin2 are obtained from the original HSV image, as shown in FIG. 14 (saturation 1400, value 1402).

Returning to FIG. 13, the two complementary images are then processed to determine the observed level of luminance L in the area of the colonies. This is achieved by calculating the mean value of the "value" component of Iin1 and Iin2 which are called respectively $L_1$ and $L_2$. Next the highest observed luminosity value is determined by:

$$L = \max(L_1, L_2)$$

The values of observed and expected Luminosity L and Lt respectively are then used to calculate an optimum exposure time in step 1310. This calculation produces a coefficient of correction (cc) to apply to the default exposure time. The coefficient is given by the equation:

$$Cc = \frac{Lt}{L}$$

Then if abs (cc−1)<0.05 the default exposure time is considered to be acceptable. Otherwise a new exposure time $T_1$ is determined as:

$$T_1 = T_0 \times cc.$$

The exposure time is then used to retake the image. This new exposure time may be stored in the exposure time database. By using this process the exposure time for a particular image is optimized automatically and provides an image which is more easily usable to analyze the sample.

A further aspect of the present invention relates to forming a vertical fusion image using the vertical illumination in the head unit. The vertical image produced is a monochrome image and includes details of the surface topography of the colonies. The images taken with a number of vertical beams bring out the absorption properties of the culture medium and colonies, as well as their relief, the reflections of light on the surfaces making pixels less or more bright depending on the texture and orientation of the surface. Two or more vertical monochrome images are taken. Indeed, as the vertical illumination produces some white (saturated) areas just below the lights, it is useful to have images from various illumination positions to see details on all areas of the sample.

In an alternative embodiment the monochrome illumination may be collimated.

In addition, a color image is taken from above with the sample being illuminated from above, by means of an internal reflection within the imaging system or from below. The source can be any of the sources found in the imaging system. The color image may be produced by applying all the color channels (RGB) at once or by sequentially obtaining an image from each channel and then combining them at an appropriate time.

The monochrome image and the color image are then combined to give color and relief information. The images are combined as follows. The two (or more) vertical images are read into the system. Combination is effected by determining the minimum intensity between two corresponding pixels, one from each of the images to be combined. This can be expressed as:

$$Iout = \min(I1, I2)$$

Figure 15A:
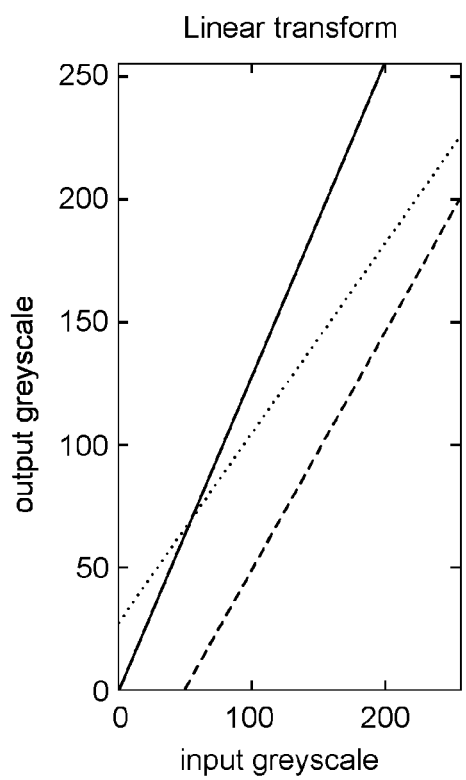
FIGS. 15a and 15b are two graphs showing possible transform functions for a still further image enhancement technique, according to one aspect of the present invention.
Figure 15B:
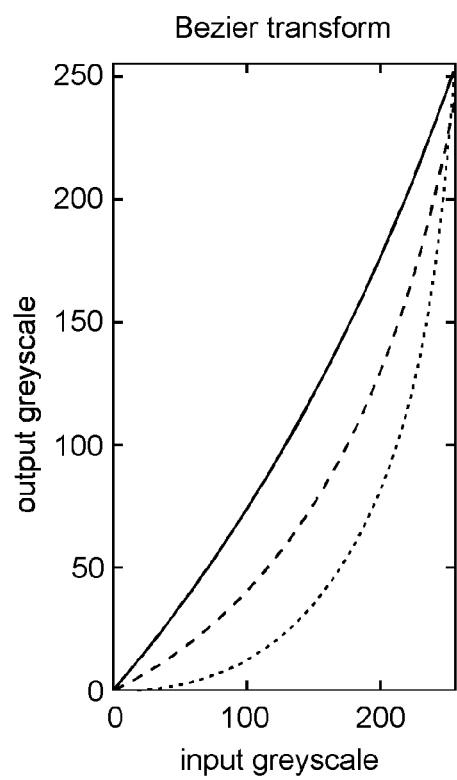

The combination of the resulting vertical image (called the combined image) to the color image will now be described in greater detail. As different illumination sources are used, the intensity in the image is linked to the intensity of the source. As such it may be necessary to adjust the contrast of the combined image. This is done by applying a transformation function to the combined image. The transformation may be a linear transformation of the type shown in FIG. 15*a* or a Bezier type transformation as shown in FIG. 15*b*. The combined image is good but can be improved still further by further processing. This may be achieved by applying a filter in the frequency domain to the monochrome image prior to combination.

The objective is to remove some of the luminance of the image without significantly modifying the color to ensure that contour information is the most noticeable feature of the final image. In order to achieve this, a discrete two dimensional Fourier transformation is applied to the monochrome image. This produces a matrix of the same size as the original image containing the complex coefficients of the transformation. The original image is the weighted sum of periodic functions of different frequencies, the weights being the coefficients of the transformation. The points in the centre of the matrix correspond to coefficients for Low frequency functions and those on the outside to coefficients for High frequency functions. The function used is:

$$If = fft2(I)$$

A frequency domain Gaussian filter is constructed and is applied to a second matrix that is equal in size to the monochrome image where the values are given by:

$$y = 1 - \exp\left(-\frac{r^2}{2*D0^2}\right)$$

where r is the Euclidian distance in pixels between a point and the centre of the matrix and Do is the filtered ray radius and is between 0 and 30 pixels. It should be noted that the pixel range is dependant on the size of the image being processed and may be different for different sized images.

The two matrices are multiplied together element by element to produce a filtered monochrome image. As the filter (first matrix) has values approaching zero in the centre the coefficients for low frequency functions in the monochrome image are dramatically reduced.

An inverse discrete Fourier transformation is applied to return the image to the spatial zone. The result is an image where the low frequencies of the image have practically disappeared. This accentuates the contours and removes certain bright spots in the image.

Figure 16:
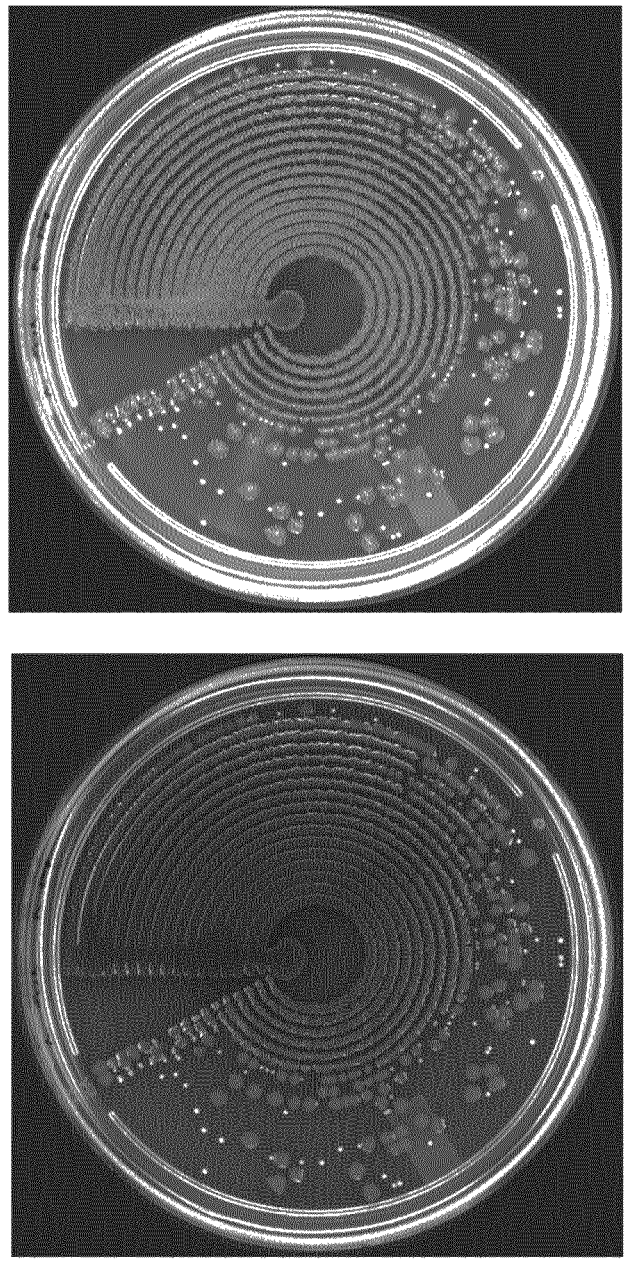
FIG. 16 is a resultant image after the still further image enhancement technique, according to one aspect of the present invention.

The color image is then combined with the processed monochrome image. This is done by adding a level of luminosity to each pixel in the color image which is a percentage of the equivalent pixel luminosity in the monochrome image. The fraction can be anywhere between 10% and 100%. The resulting image is shown in FIG. 16. In a preferred embodiment the combination of color and monochrome luminosity is achieved as follows. The luminosity of the monochrome image is combined with each of the red, green and blue channels separately pixel by pixel. This produces respectively a red, green or blue enhanced image. The red, green and blue enhanced images can then be combined to form a full color enhances image.

The weight of each of the red, green and blue enhanced images can be balanced or biased in any preferred manner. This can give different color balances, which are useful for determining different types of colonies. For example, colonies of a particular color may be more visible when illuminated with more of one color illumination than another.

The vertical fusion image produced by this aspect of the present invention provides a mechanism for readily viewing the contours and textures of colonies grown on the culture medium. The height and vertical shape of colonies are important attributes in identifying colonies. In addition, having color information included within the contour details can help in the identification process.

In a further image enhancement technique, the difference between α and β hemolysis is analyzed. To identify various species of bacteria, it is useful to harvest search bacteria on a blood culture medium in order to determine if such bacteria are alpha-hemolytic or beta-hemolytic. When alpha-hemolysis is present, the culture medium under the colonies is dark and green in color. This is sometimes called 'green hemolysis' because of the color change in the culture medium. For instance, *Streptococcus pneumoniae* and a group of oral streptococci display alpha-hemolysis. Beta-hemolysis, sometimes called 'complete hemolysis', is a complete lysis of red cells in the media around and under the colonies in the culture medium. The area appears lightened (yellow) and transparent. *Streptococcus pyogenes*, or Group A beta-hemolytic Strep (GAS), displays beta-hemolysis.

Figure 23:
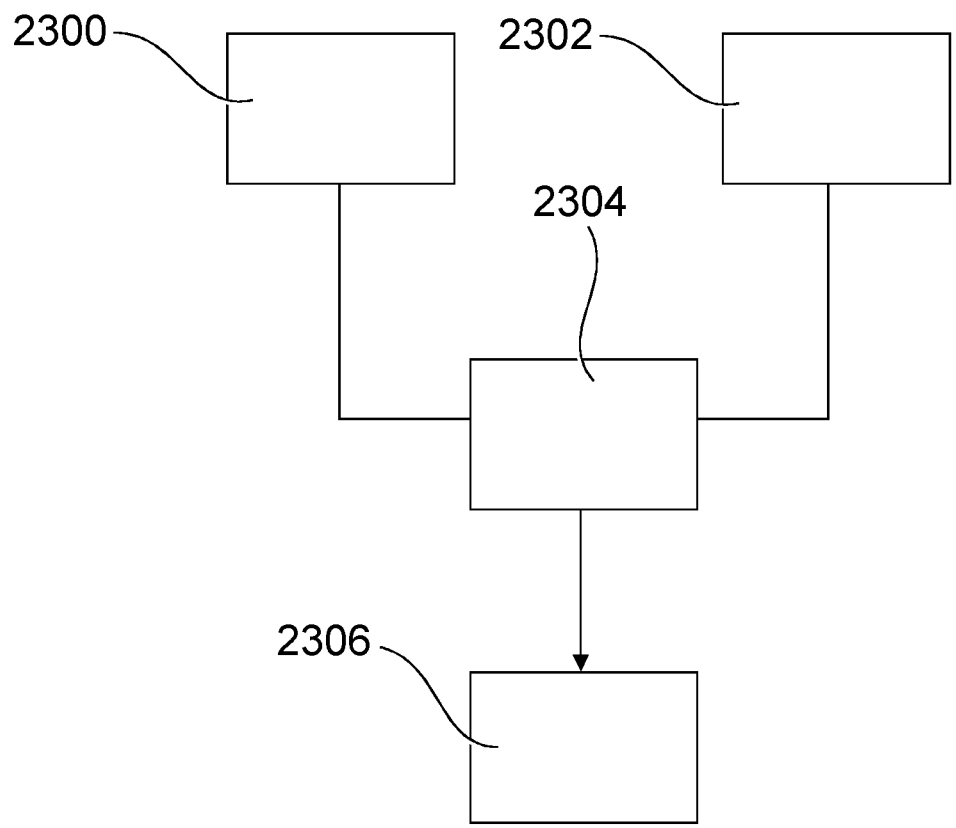
FIG. 23 is a process diagram showing the steps for an image processing technique, according to one aspect of the present invention.

It is therefore necessary to be able to identify alpha and beta hemolysis, with realistic color information, for on-screen viewing of Petri dishes by biologists. It is an object to combine two images having different features by a method that will produce realistic colors and visual identification of hemolysis for on-screen viewing of Petri dishes by biologists. A first image is taken with an illumination source such as an annular beam at step 2300 on FIG. 23. A second image is taken with an illumination source such as a backlight illumination at step 2302. The resultant images are combined in step 2304 based on a fusion algorithm. An example of a fusion algorithm used is the "exposure fusion" algorithm proposed by Mertens et al (Pacific Graphics 2007—http://research.edm.uhasselt.be/~tmertens/). In the present invention, this algorithm is not only applied to images with different exposure time but also to images which have been illuminated from different directions. In the particular case of the "exposure fusion" algorithm, the algorithm requires three weight parameters to be applied depending on the required combined image. Examples of the parameters are contrast, saturation and degree of exposure. For the imagining of α and β hemolysis, the value of each above mentioned parameters are set to be 1. The resultant image 2306 gives a full color image having detailed contour information which then can be used to distinguish α-hemolysis from β-hemolysis.

Figure 17:
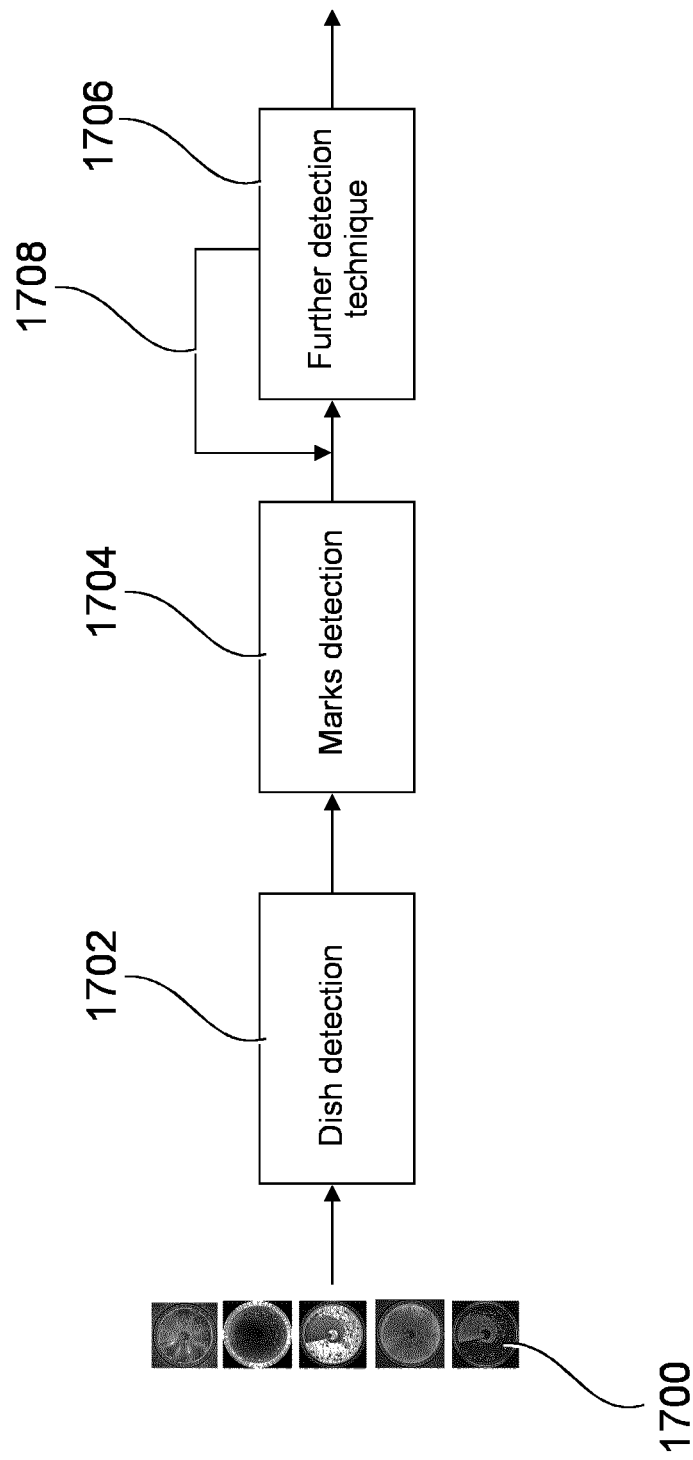
FIG. 17 is an example of an image processing technique, according to one aspect of the present invention.

In a further embodiment a number of additional image processing techniques will now be described. FIG. 17 shows a simplified view of a generic image processing technique. In a first step 1700, a plurality of images is taken from one or a combination of the illumination source. A dish detection technique step 1702 is carried out to detect a first type of characteristics of the dish such as the contours and edges of the dish. Then in a step 1704 a mark detection technique is carried out to identify a second type of characteristics such as marks or serigraphy on the dish. In a step 1706 a further detection technique is carried out. There are a number of different further detection techniques which will be described in greater detail below which relate to the detection of biological objects or colonies. There may be a sequence of different image processing techniques carried out on the same sample and if this is the case the process will feedback in step 1708 to a subsequent further image processing technique. In some of the further detection techniques it may not be necessary to carry out dish detection and/or mark detection as these may not assist in the further detection technique being carried out. As such at least some of the further detection techniques may be stand alone techniques.

The dish detection technique 1702 is a technique which identifies the rings of the Petri dish formed by the walls and the lid thereof. The technique involves an object detection technique, such as a circular Hough transformation (as described in: Duda, R. O. and P. E. Hart, "Use of the Hough Transformation to Detect Lines and Curves in Pictures," *Comm. ACM, Vol.* 15, pp. 11-15 (January, 1972) to detect circular objects of a predetermined size. A backlight image is used as this gives a well contrasted image of the sample. In addition, the size of the Petri dish is entered to indicate to the transformation the nature of the circular object or objects being sought. The number of rings being sought may also be entered so that the various rings of the dish and the lid can be located as appropriate. The application of the Hough transformation could result in localization of one or more of the rings (lid or main body) of the Petri dish. In a further step, this information could enable the removal of the Petri dish rings or masking of the rings or the exterior of the dish from a resultant image, if required. This ensures that further detection methods can focus on the interior of the Petri dish. It should be noted that the Hough transformation applies to circular vessels; however other object detection algorithms may be used for vessels which are different shapes.

Alternatively, another kind of object detection technique can be applied to detect the contours of the Petri dish without using the circular Hough transformation. The alternative object detection technique allows retrieving a closed contour in the image to identify the border of the Petri dish. The alternative technique comprises a first step of retrieving the potential contour of the image based on a well-known technique such as the Canny edge detection method described in the document "A Computational Approach to Edge Detection" by J. Canny or the morphological gradient edge detection. Thus, the first step provides a grayscale image.

The alternative technique comprises a second step of filling the retrieved contours using a Matlab™ function such as "imfill with holes option". This means that the filling step only fills the interior of the dish in the situation where the contours are closed contours around the dish. The alternative technique further comprises a step of retrieving the largest inscribed circle within the closed contour. In a further step the plate radius and the location of the centre of the dish are determined based on the corresponding radius and location of the centre of the inscribed circle. The advantage of the alternative technique is that no predetermined size of the contour needs to be known in advance to carry out this object detection technique.

Figure 18:
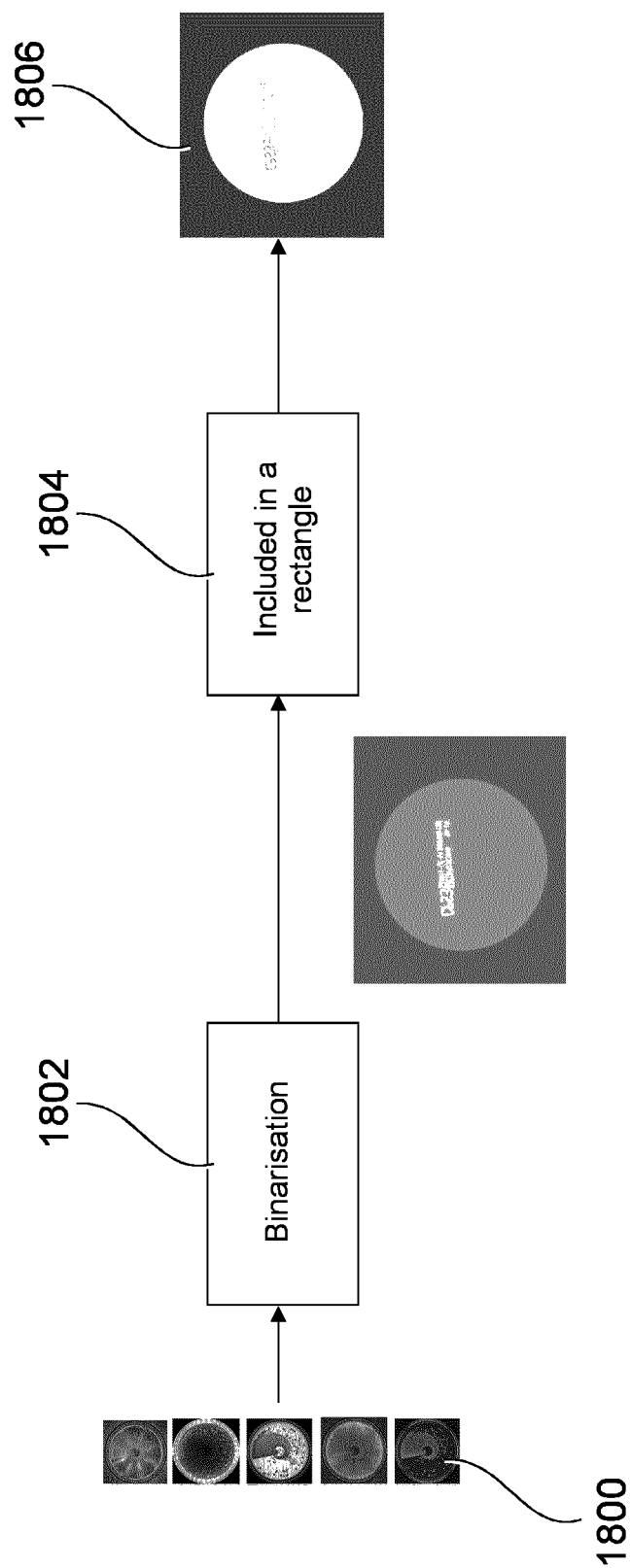
FIG. 18 is a process for mark detection, according to one aspect of the present invention.

Referring to FIG. 18, the mark detection technique is now described. In a first step 1800 a plurality of images of a Petri dish are loaded into the system. A segmentation process operates in step 1802 wherein the images are segmented in a binarization process in step 1802 to form a digitized image. The segmentation process provides a separation of pixels into a plurality of classes. The binarization process is a specific segmentation process which provides two classes of pixels, either black or white. The binarization process is based on the original structure of the serigraphy which is made of ink point of dark color. Thus, the binarization process comprises steps for retrieving objects having a point shape and a dark color. As a result, the binarization process provides an improved method for distinguishing serigraphy from other objects such as colonies, bubbles or defaults. The binarization process of step 1802 comprises several steps for identifying serigraphy on the Petri dish. The binarization process differs from the well-known K-means clustering method. The k-means clustering method gathers pixels having the same color. The binarization process gathers pixels having similar color and also being in close vicinity. A search can be made to identify objects that are for example substantially rectangular in shape in step 1804. More generally a search may be made for and features or objects that present non-biological characteristics. These features could include particular shapes, serigraphy, bar codes, tickets, labels etc. The identified objects are marked and assumed to be marks on the Petri dish. The resultant image is 1806 and can be used to localize and if needed remove or mask marks on the dish, irrespective of the original image. The position of the mark can be used in all other images of the same dish, whatever the illumination, irrespective of the image or set of images used to detect the marks in the first instance. In a particular example this algorithm may be used to identify the marks when the dish appears to have no colonies therein.

Figure 19:
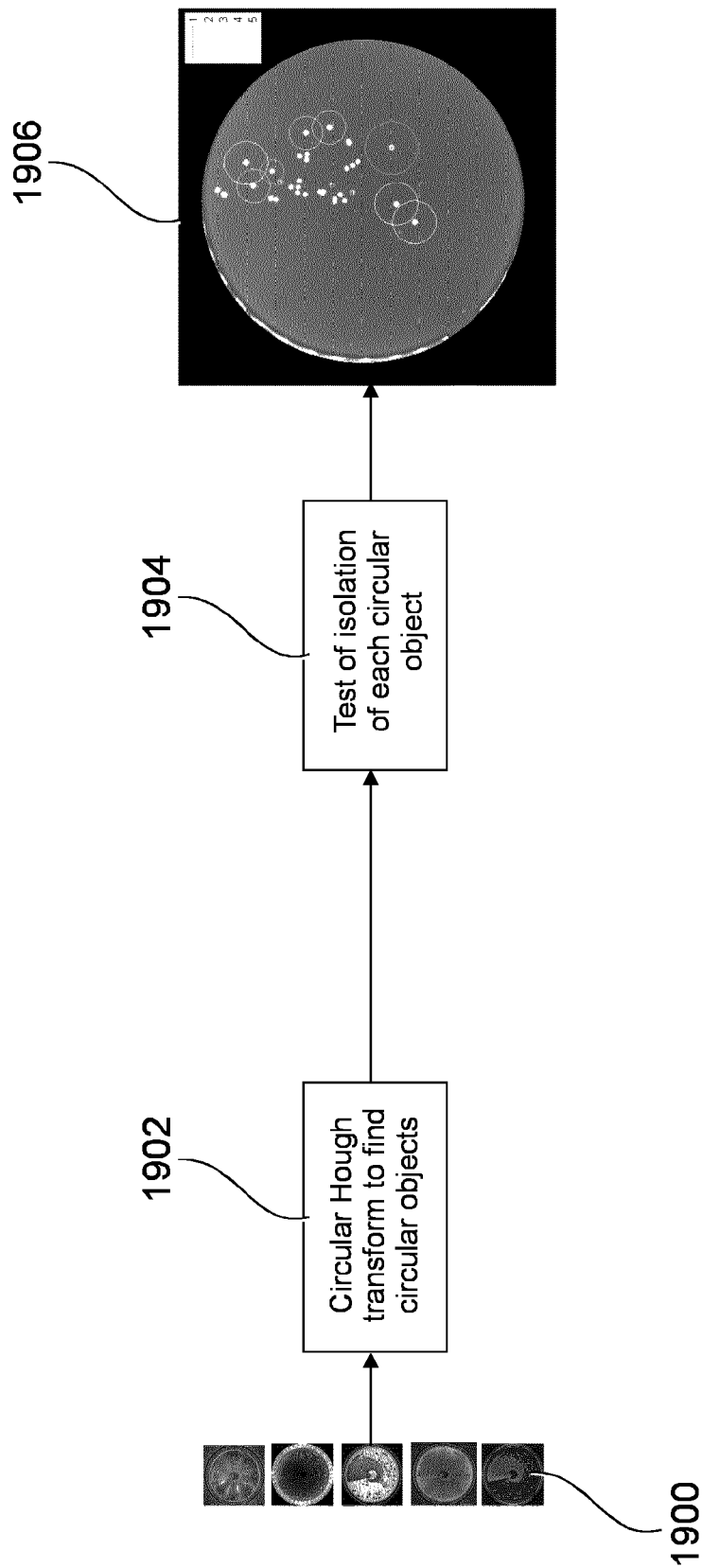
FIGS. 19 and 19a are process diagrams showing the steps for an image processing technique, according to one aspect of the present invention.
Figure 19A:
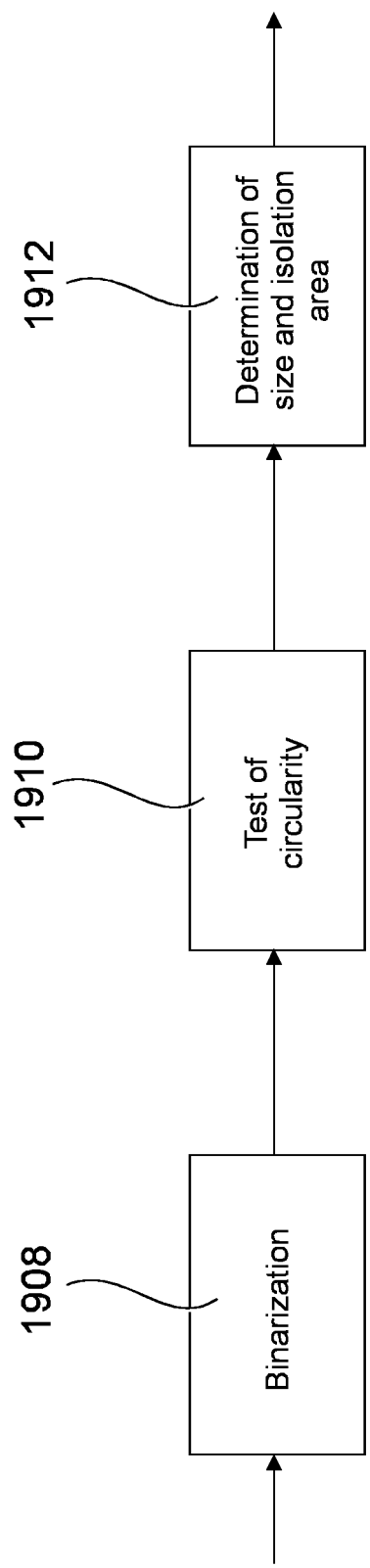

Certain further image processing techniques will now be described. FIGS. 19 and 19a show a process for detecting isolated colonies. In a first step 1900, a plurality of images is taken using different illumination sources. One image or a combination of the images is selected for further processing. The selected image or images are then processed by applying a circular Hough transformation in step 1902. This identifies circular objects, such as colonies of bacteria. A typical colony size may be entered to limit the Hough transformation to search for circular elements of a specific size. Once circular objects (colonies) have been identified an isolation test is applied to each circular object at step 1904. The isolation test is further described with reference to FIG. 19a. The isolation test includes the step of determining the centre of the identified circular object (not shown). A binarization step 1908 is then applied to obtain a binarized image wherein the centre of the binarized image corresponds to the centre of the identified circular object. Thereafter, a test of circularity is carried out in step 1910 on the binarized image to verify if the binarized object is circular. A further step of determination of size and isolation area 1912 is carried out to determine the size of the colony as well as the diameter of the colony and the area of isolation around the colony. A typical output is shown as 1906.

Figure 20:
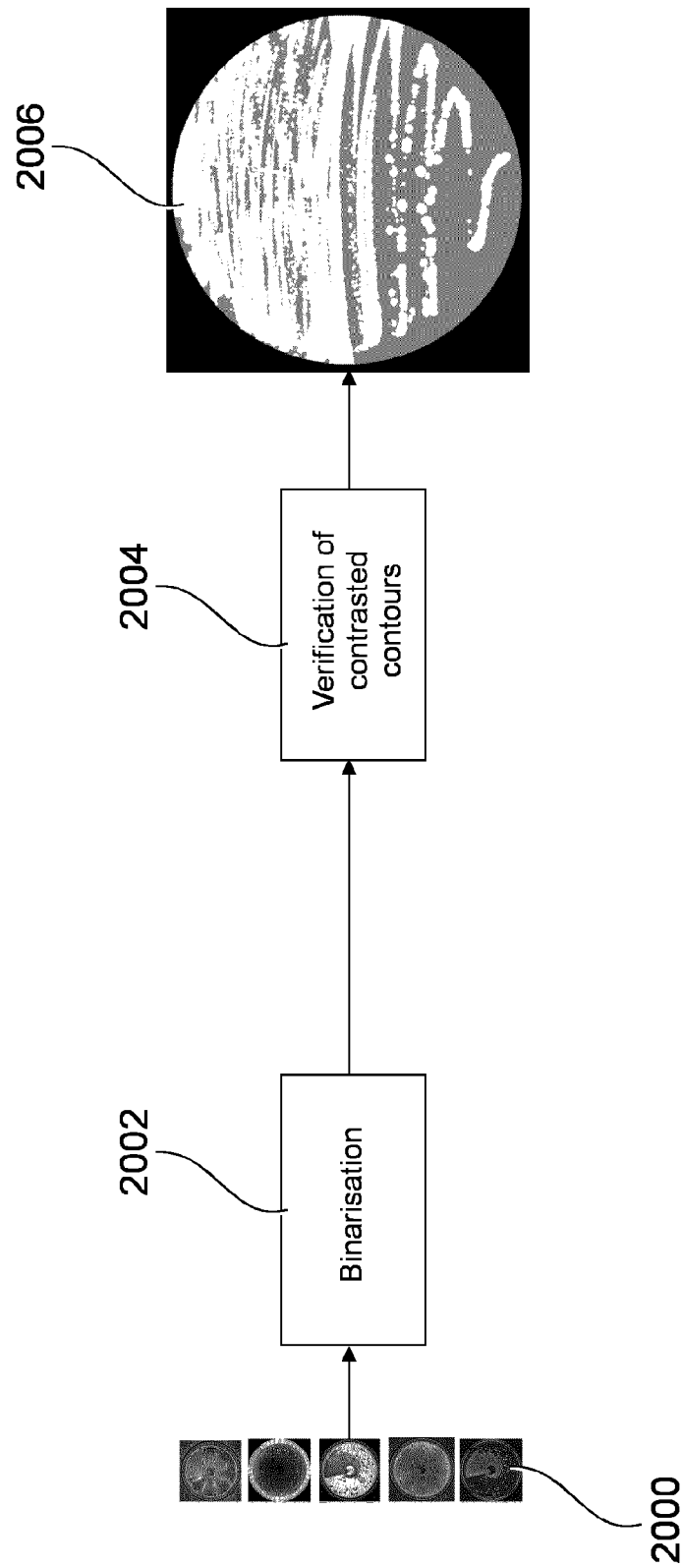
FIG. 20 is a process diagram showing the steps for an image processing technique, according to one aspect of the present invention.

In a further image processing technique, detection of large masses of colonies is carried out. This is shown with reference to FIG. 20. In a first step 2000, a number of images are obtained using one or more different illumination beams. A predetermined image or combination of images is binarized at step 2002 to form a digitized image. The digitized image is analyzed to determine if the contours of objects on the digitized image correspond to high contrast zones in the original image or images. This analysis is performed by comparing zones of contours in the digitized image and zones of high contrast, such as areas having a gradient greater than 10, in the original image or images (step 2004). If the correspondence is sufficient, we consider that digitized objects correspond to masses of colonies and an output 2006 is produced. This output can be used to identify areas having a high density of colonies or colonies that are not circular in nature. Alternatively, another technique for detecting large masses of colonies may be carried out. The alternative technique relates to a region-based segmentation instead of color-based segmentation. Thus, the region-based segmentation provides a plurality of classes of pixels to identify objects. The pixels are gathered based on a predetermined criterion such as color, contrast. The region-based segmentation is an iterative method to put together pixels being spatially close and homogeneous based on the predetermined criterion. As a result, there is no limit related to the number of classes.

Figure 21:
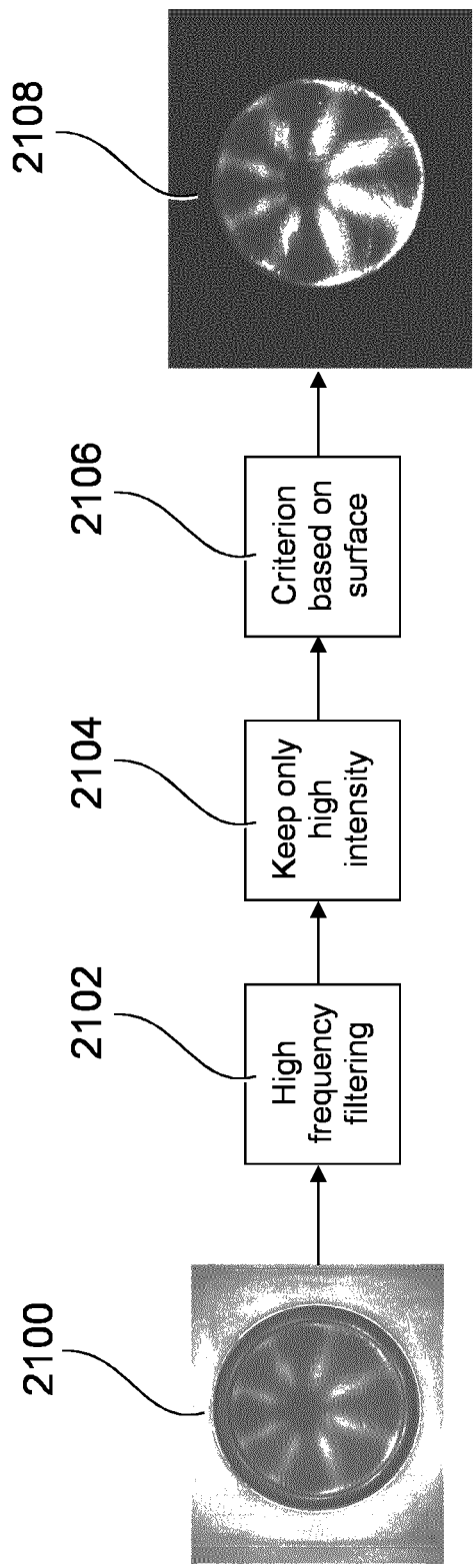
FIG. 21 is a process diagram showing the steps for an image processing technique, according to one aspect of the present invention.

FIG. 21 shows a process for identifying swarming. Swarming is a rapid and coordinated movement of a bacterial population across the culture medium. Swarming is another indication of the existence of growth of colonies, but is less visible. In a first step 2100 an image is obtained which contains contour or relief information. A typical image may be a vertical image or a lateral annular image or any other image or combination of image. A process 2102 is applied to the image in which only zones of texture with high frequency are retained in the image. The high frequencies are present in zones of rich texture and the swarming is characterized by "waves" on the surface of the dish visible on images highlighting relief. In order to only keep zones of high frequency and texture, two steps are necessary. In a first step, a low pass filter is applied to the original image. An example of such a filter is a median filter 7×7 as shown in FIG. 22 which applied to each point on the image. In a second step the original image is subtracted from the low pass filtered image to highlight zones of high frequency (texture) and not sharp contours. The image obtained may be referred to as a textured image. In order to characterize the presence of swarming and to determine whether swarming is visible a criterion based on a "quantification" of zones of texture is used. In step 2104 the high intensity regions of the original image are maintained in order to keep only zones of information (relief) in the original image. A coefficient relating to the amount of texture is determined by the mean of the value of the texture image for high intensity zones in the original image. If the coefficient is equal to or above a certain threshold in step 2106, swarming is identified and if the coefficient is below the threshold, there is no swarming. The resultant image is shown as 2108 and could enable identification of areas of swarming.

FIG. 8 is a table which identifies specific examples of the optimal illumination source or sources to detect specific characteristics in different culture media. The table shows that for different culture media, such as COS (an opaque medium) and CPS, (a transparent/semitransparent medium), different illumination sources may be more appropriate. The table also shows a number of examples of detection processes carried out after creation of the image. For each example the combination of illumination sources or beams are shown.

In order to detect isolated colonies a combination of backlight, annular and inverted annular produces the best results for a CPS culture. Whereas for a COS culture only backlight and annular produce the better result. The table shows a number of other examples.

With reference to FIGS. 24 and 25, as previously mentioned, there is shown an example of a robotic arm. As shown in FIGS. 24 and 25, the robotic arm comprises a first, generally vertical guide 2401 and a second generally horizontal guide 2402. The first guide 2401 is adapted to guide a carriage 2410 in a vertical direction. The carriage 2410 comprises a support 2411 which is adapted to receive and retain an assembly of a Petri plate and a lid for the Petri dish in an upside-down position.

In FIG. 24 the carriage 2410 is shown with the Petri dish lid 2430 upside-down retained between a finger 2412 and a movable gripper 2413. The gripper 2413 is arc shaped and adapted to push the Petri dish lid 2430 against the finger 2412 to hold the Petri dish lid 2430 in between the finger 2412 and the gripper 2413 during the displacement of the carriage 2410. The gripper 2413 is attached to the end of an arm 2414 for moving the gripper 2413 between the holding position as shown in FIG. 24 and a release position for releasing the Petri dish lid 2430. The second guide 2402 is adapted to guide a carriage 2420 in a horizontal direction. The carriage 2420 comprises a first part 2421 for sliding along the guide 2402 and a second part 2422, which is rotatable over at least 180° with respect the first part 2421. The second part 2422 of the carriage 2420 is provided with an arc shaped gripper 2423.

The gripper 2423 is adapted to push a Petri plate 2431 against a finger 2424 in order to hold the Petri plate 2431 in between the finger 2424 and the gripper 2423. The gripper 2423 is attached to the end of an arm 2425 for moving the gripper 2423 between the holding position as shown in FIG. 24 and a release position for releasing the Petri plate 2431.

The functioning of the robotic arm according to FIGS. 24 and 25 is as follows: the carriage 2410 is adapted to receive an assembly of a Petri plate 2431 and a lid 2430 in a first position wherein the assembly is in an upside-down position. From this first position the carriage 2410 is able move the assembly of the Petri plate 2431 and the lid 2430 vertically upwards. The carriage 2410 will move the assembly upwards to a position to allow the gripper 2423 to push the Petri plate 2431 against the finger 2424. Once the Petri plate 2431 is retained in between the gripper 2423 and the finger 2424, the carriage 2410 moves downwards, separating the Petri plate 2431 and the lid 2430. The Petri plate 2431 is then rotated, by rotating the second part 2422 of the carriage 2420 with respect to the first part 2421 thereof.

In FIG. 25, the Petri plate 2431 is shown in an intermediate position, with the second part 2422 of the carriage 2420 being rotated over 90° with respect to the first part 2421.

From the position according to FIG. 25 the rotational movement is continued until the Petri plate 2431 reaches a top open, horizontal position. After the rotational movement of the Petri plate 2431 or during this rotational movement, the first part 2421 of the carriage 2420 is moved along the guide 2402 towards a position for taking an image of the content of the Petri plate 2431. This position is indicated in FIG. 24 with reference number 2450. Once the image, or a series of images, of the Petri plate 2431 has been taken, the movement of the carriages 2410 and 2420 can be inverted in order to return the assembly of the Petri plate 2431 and the lid 2430 to a release position for off loading the assembly.

Figure 27:
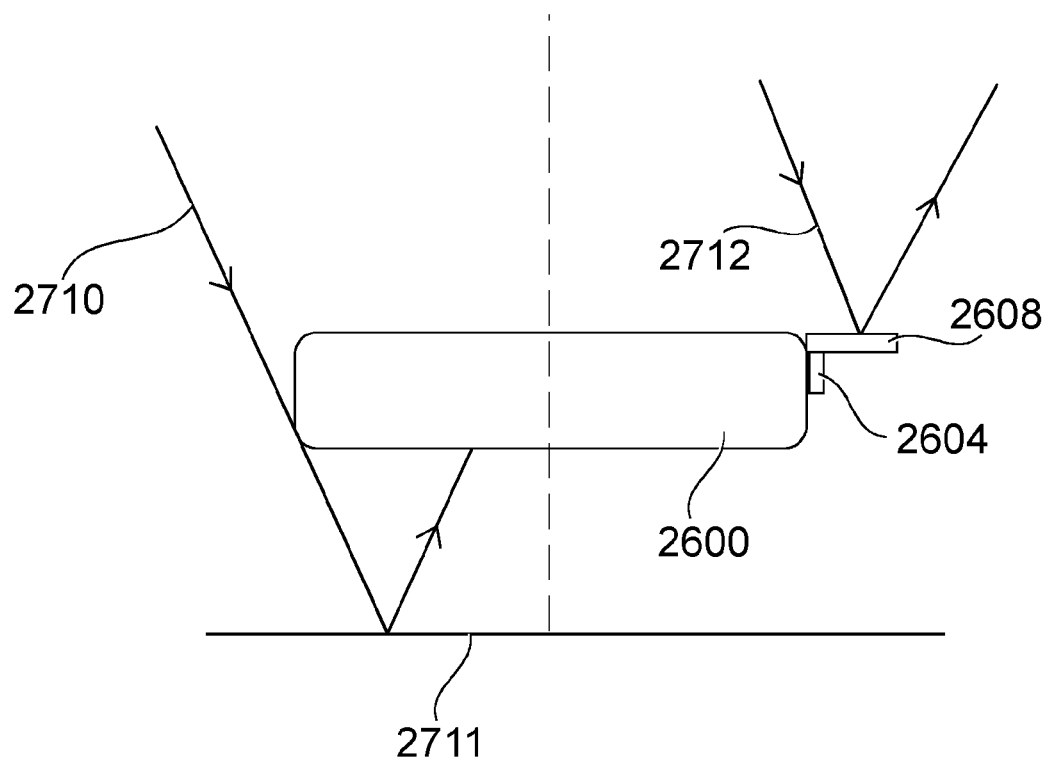
FIG. 27 is a cross sectional view of the Petri dish provided with the mask during annular illumination, according to one aspect of the present invention.

With reference to FIGS. 26 and 27, as previously mentioned, now will be described how the mask operates. As shown in FIG. 26, when the Petri plate 2600 is located over the wheel, the gripper 2604 of the robotic arm surrounds partially the contours of the Petri plate 2600. As a result, lines 2602 represent parts of the contours of the plate which are not covered by the gripper 2604. When annular illumination is provided on the Petri plate for taking an image of the interior of the Petri plate, as shown in FIG. 27, a light beam 2710 may be reflected on the surface 2711 located below the Petri plate. The light beam may then be reflected back to the Petri plate 2600 as an interference beam. As a result, when taking an image, the interference beam may produce corresponding interferences in the taken images of the interior of the Petri plate. As shown in FIG. 26, a mask 2608 may be provided around the contour of the Petri plate. The mask 2608 totally surrounds the contours of the Petri plate 2600. The width of the mask is adapted to be higher than the width of the gripper 2604. FIG. 27 shows two configurations of the Petri plate separated by the dotted line. On the left hand side of the dotted line the Petri plate is not provided with the mask 2608. On the right hand side of the dotted line, the Petri plate is provided with the mask 2608 which covers the gripper 2704. In the first configuration, during annular illumination, when a beam 2712 illuminates a zone near the Petri plate 2600, the beam 2712 is reflected by the surface 2711 and produces an interference beam which reaches the bottom part of the Petri plate. In the second configuration, during annular illumination, when a beam 2712 illuminates a zone near the Petri plate, such as the surface of the mask, the mask 2608 prevents any interference beam to illuminate the interior of the Petri plate 2600 or to interfere with the images being taken.

It will be appreciated that other combinations of detection processes and optimal illumination sources may also be used. The positions of the illumination sources may be varied as required and are not fixed to the locations and direction of impact as described herein.

It is anticipated that the various enhancement and image processing techniques may be combined to analyze certain samples. This could entail using some or all of the techniques. The techniques may be applied in any sequence and the sequence may vary from one sample to the next. After the selected technique or techniques have been applied to a sample and no colonies have been identified it may be determined that the sample has no colonies which have grown thereon.

In any image enhancement technique or image processing technique the system may be provided with additional information at the start of the process. This additional information includes details relating to the Petri dish or other sample container such as sizes, shapes, materials, etc. The additional information may also include details of the culture media and any expected type of material that might be growing thereon. The information may also include imaging details such as exposure time, illumination source, orientation of the Petri dish, any other optical or control parameters, etc. The information may indicate the purpose of the application, e.g. industrial, medical, etc. Any other relevant information may also be included as appropriate.

This automated process of analyzing a sample and detecting artifacts offers many advantages. The ability to detect and, if necessary, remove artifacts, such as writing and marks, makes isolation of colonies easier. The same technique could be used to detect other artifacts and in an additional step to remove them from the image. For example, if a batch of dishes has excess bubbles in the nutrient of a certain size and color, these artifacts may be detected by means of the above described process and if necessary removed. Similarly, other optical artifacts can also be treated.

The above described inventions relate to systems and methods for obtaining and processing images of biological samples. Some or all of the aspects of the present invention is could be used in different environments.

Some of the above described inventions relate to processes which can be carried out at least to some extent on a computer. Accordingly, reference to processing and steps can be carried out by means of software or hardware or any combination thereof. Wherein aspect of the invention has been described with respect to hardware it will be appreciated that it can be a replaced by an appropriate software module. Similarly, software modules or processes can be replaced with appropriate hardware.

It will be appreciated there are many possible variations of the present invention which would fall within the intended scope of the invention.

The invention claimed is:

1. An imaging system for generating images of biological samples having a surface, the imaging system comprising:
    a sample holding unit comprising a sample drawer for supporting a biological sample in use;
    a plurality of illumination sources, the plurality of illumination sources being arranged around the sample holding unit and each illumination source of the plurality of illumination sources adapted to illuminate the biological sample, in use, from a different direction;
    a camera for capturing illumination which has impinged on the biological sample to thereby form an image of the biological sample;
    wherein at least one illumination source of the plurality of illumination sources is arranged in a direction that is not perpendicular to the surface of the biological sample; and
    wherein the plurality of illumination sources comprises three or more of a backlighting source, a horizontal source, an annular source directed towards the surface, an annular source directed upwards, away from the surface, and a vertical source.

2. The system of claim 1, wherein directions of at least two of the illumination sources of the plurality of illumination sources are substantially not coplanar.

3. The system of claim 1, wherein the plurality of illumination sources are used to produce a plurality of images, which images can be combined to form a composite resultant image.

4. The system of claim 1, wherein different combinations of the plurality of illumination sources can be used to produce different images for different biological analyses.

5. The system of claim 1, wherein each illumination source of the plurality of illumination sources is included in a unit and wherein each unit can be stacked one on top of another.

6. The system of claim 5, wherein the units are moveable relative to one another.

7. The system of claim 1, wherein the biological sample is movable relative to the plurality of illumination sources.

8. The system of claim 1, wherein the plurality of illumination sources comprise red, green, blue sources, white light sources or UV sources.

9. The system of claim 1, wherein the biological sample is capable of being illuminated by a horizontal source.

10. The system of claim 1, further comprising a processing system for enhancing or processing images to effect a biological analysis of the biological sample.

11. The system of claim 1, further comprising an incubator system for incubating the biological samples prior to imaging the biological samples.

12. An incubator for incubating the biological samples including an imaging system according to claim 1.

13. A method of generating images of biological samples wherein the biological sample has a surface, the method comprising:
    illuminating a biological sample with a plurality of illumination sources, the plurality of illumination sources being arranged around a sample holding unit and each illumination source of the plurality of illumination sources being adapted to illuminate the biological sample, in use, from a different direction, wherein the sample holding unit comprises sample drawer adapted to hold the biological sample;
    capturing illumination which has impinged on the biological sample to thereby form an image of the biological sample;
    wherein the step of illuminating comprises illuminating the biological sample with at least one illumination source of the plurality of illumination sources, which at least one illumination source is directed in a direction which is not perpendicular to the surface of the biological sample; and
    wherein the plurality of illumination sources further includes at least two additional illumination sources selected from the group consisting of: a backlighting source, a horizontal source, an annular source directed towards the surface, an annular source directed upwards, away from the surface, and a vertical source.

* * * * *